United States Patent [19]
Dietz et al.

[11] Patent Number: 5,888,398
[45] Date of Patent: Mar. 30, 1999

[54] COMPOSITION AND PROCESS FOR SEPARATING CESIUM IONS FROM AN ACIDIC AQUEOUS SOLUTION ALSO CONTAINING OTHER IONS

[75] Inventors: Mark L. Dietz, Elmhurst; E. Philip Horwitz, Naperville, both of Ill.; Richard A. Bartsch, Lubbock, Tex.; Richard E. Barrans, Jr., Downers Grove; David Rausch, Naperville, both of Ill.

[73] Assignee: ARCH Development Corp., Chicago, Ill.

[21] Appl. No.: 789,653

[22] Filed: Jan. 27, 1997

[51] Int. Cl.$^6$ .......................... B01D 11/00; B01D 11/02; C01D 17/00; C07D 323/00

[52] U.S. Cl. .......................... 210/634; 210/638; 210/639; 210/682; 210/685; 210/688; 423/2; 423/181; 549/349

[58] Field of Search ................................. 210/634, 638, 210/639, 682, 688, 685; 423/2, 8, 10, 179, 181, 182, 201, 202, 157; 549/349

[56] References Cited

U.S. PATENT DOCUMENTS

| | | | |
|---|---|---|---|
| 4,749,518 | 6/1988 | Davis, Jr. et al. | 252/627 |
| 5,100,585 | 3/1992 | Horwitz et al. | 252/631 |

OTHER PUBLICATIONS

Ross and White, *Anal. Chem.*, 36:1998 (1964).
Egan, et al., *Inorg. Chem.*, 4:1055 (1965).
Arnold, et al., *Ind. Eng. Chem. Process. des. Dev.*, 4:249 (1965).
Roddy and Coleman, *Inorg. Nucl. Chem.*, 35:4271 (1973).
Kyrs, et al., *Coll. Czech. Chem. Commun.*, 25:2642 (1960).
Slater, *Nucl. Sci. Eng.*, 17:576 (1963).
Crowther and Moore, *Anal. Chem.*, 35:2081 (1963).
Rais, et al., *J. Inorg. Nucl. Chem.*, 38:1376 (1976).
Koprda, et al., *J. Radioanal. Nucl. Chem.*, 80:55 (1983).
Blasius and Nilles, *Radiochem. Acta*, 36:207 (1984).
Parish, et al., *J. Org. Chem.*, 43:4577 (1978).
Gerow, et al., *Sep. Sci. Technol.*, 16(5):519–548 (1981).
Schulz and Bray, *Sep. Sci. Technol.*, 22:191–214 (1987).
Kinard, et al, *Sep. Sci. Technol.*, 15:1013 (1980).
Kinard and McDowell, *J. Inorg. Nucl. Chem.*, 43:2947 (1981).
McDowell, et al., *Solvent Extr. Ion Exch.*, 4:217 (1986).
Blasius and Nilles, *Radiochim. Acta*, 35:173 (1984).
Shuler, et al., *Solvent Extr. Ion Exch.*, 3:567 (1985).
McDowell, *Sep. Sci. Technol.*, 23:1251 (1988).
McDowell, et al., *Anal. Chem.*, 64:3013–3017 (1992).
Strzelbickl and Bartsch, *Anal. Chem.*, 53: 1894 (1981).
Brown and Bartsch, "Ion Extraction and Trasport by Proton–Ionizable Crown Ethers", *Inclusion Aspects of Membrane Chemistry*, T. Osa and J.L. Atwood, eds., Kluwer Academic Publishers (Boston: 1991), pp. 1–57.
McDowell, et al., *Sep. Sci. Technol.*, 18:1483 (1983).
Horwitz, et al., *Solvent Extr. Ion Exch.*, 8:199 (1990).
Dietz, et al., *Solvent Extr. Ion Exch.*, 14:1–12 (1996).
Stott, et al., *J. Org. Chem.*, 45:4716 (1980).
Gerow, "The Use of Macrocyclic Polyethers to Remove Cesium–137 from Acidic Nuclear Wastes by Solvent Extration", Doctoral Dissertation, University of South Carolina, Columbia, S.C. (1980).

*Primary Examiner*—John Kim
*Attorney, Agent, or Firm*—Welsh & Katz, Ltd.

[57] ABSTRACT

A crown ether cesium ion extractant is disclosed as is its synthesis. The crown ether cesium ion extractant is useful for the selective purification of cesium ions from aqueous acidic media, and more particularly useful for the isolation of radioactive cesium-137 from nuclear waste streams. Processes for isolating cesium ions from aqueous acidic media using the crown ether cesium extractant are disclosed as are processes for recycling the crown ether cesium extractant and processes for recovering cesium from a crown ether cesium extractant solution.

17 Claims, 4 Drawing Sheets

COMPOSITION AND PROCESS FOR SEPARATING CESIUM IONS FROM AN ACIDIC AQUEOUS SOLUTION ALSO CONTAINING OTHER IONS

GOVERNMENTAL SUPPORT AND RIGHTS

This invention was made with government support pursuant to Contract No. W-31-109-ENG-38 with the U.S. Department of Energy. The Government has certain rights in this invention.

TECHNICAL FIELD

The present invention relates to a chemical composition that is useful for the separation of cesium ions from an acidic aqueous solution, and more particularly to a composition and process for the separation and recovery of cesium ions from acidic waste streams in a liquid/liquid separation process such as an extraction process.

BACKGROUND ART

Cesium-137 constitutes a major source of radioactivity in nuclear waste streams, such as the high level liquid wastes of nuclear fuel reprocessing solutions. Selective removal of this radionuclide from the aqueous acidic nuclear waste streams would greatly simplify their handling and ultimate disposal.

Various processes for the separation of cesium ions are known in the art. These processes include selective ion precipitation, ion exchange using solid materials, and solvent extraction processes that are also referred to as liquid/liquid separation processes.

For separating cesium ions from other alkali metal ions in very basic solution, solvent extraction methods have been known for many years. Ross and White, *Anal. Chem.*, 36:1998 (1964); Egan, et al., *Inorg. Chem.*, 4:1055 (1965); Arnold, et al., *Ind. Eng. Chem. Process. Des. Dev.*, 4:249 (1965); and Roddy and Coleman, *Inorg. Nucl. Chem.*, 35:4271 (1973). Other solvent extraction methods for cesium ion separation have been reported in the art. Kyrs et al, *Coll. Czech. Chem. Commun.*, 25:2642 (1960); Slater, *Nucl. Sci. Eng.*, 17:576 (1963); Crowther and Moore, *Anal. Chem.*, 35:2081 (1963); Rais, et al., *J. Inorg. Nucl. Chem.*, 38:1376 (1976); and Koprda, et al., *J. Radioanal. Nucl. Chem.*, 80:55 (1983).

More recently, solvent extraction methods have been reported for the recovery of cesium ions from acidic solutions. Blasium and Nilles, *Radiochem. Acta*, 36:207 (1984); Gerow, "The Use of Macrocyclic Polyethers to Remove Cesium-137 from Acidic Nuclear Wastes by Solvent Extraction", Doctoral Dissertation, University of South Carolina, Columbia, S.C. (1980); Gerow et al., *Sep. Sci. Technol.*, 16(5):519–548 (1981).

None of the processes described to date has proven entirely satisfactory when cost, safety, engineering and performance considerations are all taken into account. Schulz and Bray, *Sep. Sci. Technol.*, 22:191 (1987).

Several factors affect the choice of a system for a solvent extraction process to separate cesium ions from aqueous acidic media. These factors include the choice of the cesium ion extractant, the composition of the aqueous and organic phases ("the extraction system"), the chemistry of the extraction process, and the practicality of the full-scale process.

The cesium ion extractant should be soluble enough in the organic solution ("organic phase") to provide a sufficiently high extractant concentration, and thereby cesium ion concentration in the organic phase. The cesium ion extractant should be relatively insoluble in the acidic aqueous solution ("aqueous phase"). It should be possible to separate the cesium ions from the extractant after use to permit recycling of the cesium ion extractant and recovery of the cesium ions.

The extraction system should be such that the distribution of cesium ions between the organic and aqueous phases (denoted by the distribution ratio, $D_{Cs}$, described in detail hereinafter in "Materials and Methods") heavily favors the organic phase over the acidic aqueous phase to permit complete removal of the cesium ions from the acidic aqueous solution. The extraction system should also be such that the distribution of cesium ions between the organic and aqueous phases favors the aqueous phase over the organic phase under extractant recycling and cesium ion recovery conditions. The extraction system should further permit sufficient extraction of cesium ions in the presence of competing ions in the aqueous phase. The extraction system should be easy to handle and control, as well as be chemically compatible with nuclear fuel reprocessing processes.

One of the major problems encountered in the development of a workable liquid/liquid extraction process for the separation of cesium ions from aqueous acidic media is the limited solubility of many potential cesium ion extractants in solvents of low polarity that constitutes the organic phase. Another major problem is the loss of the cesium ion extractant due to its solubility in the aqueous phase. Yet another major problem is finding an extractant that permits efficient and selective extraction of the cesium ions from solutions containing high concentrations of common mineral acid anions, such as nitrate and chloride. Few processes have been able to satisty this last problem. Schulz and Bray, *Sep. Sci. Technol.*, 22:191 (1987).

The chemistry of the cesium ion further complicates the solution of these problems. The cesium(+1) ion has a low charge density due to its large ionic radius and low charge. As a result, the energy associated with bond formation between the cesium ion and the functional groups of the organic extractants is typically insufficient to completely dehydrate the cation and to strip away the water molecules associated with the anion that must accompany the cation into the organic phase to maintain electrical neutrality. Schulz and Bray, *Sep. Sci. Technol.*, 22:191 (1987). For this reason, liquid/liquid cesium ion extraction usually involves the transfer of a complex bearing a number of associated water molecules into an organic solvent.

To compensate for this charge density effect, several workers have proposed the use of macrocyclic polyethers ("crown ethers") as extractants. Kinard, et al., *Sep. Sci. Technol.*, 15:1013 (1980); Kinard and McDowell, *J. Inorg. Nucl. Chem.*, 43:2947 (1981); McDowell, et al., *Solvent Extr. Ion Exch.*, 4:217 (1986); Blasius and Nilles, *Radiochim. Acta*, 36:207 (1984); Blasiums and Nilles, *Radiochim. Acta*, 35:173 (1984); Shuler, et al., *Solvent Extr. Ion Exch.*, 3:567 (1985); McDowell, *Sep. Sci. Technol.*, 23:1251 (1988); and McDowell, et al., *Anal. Chem.*, 64:3013 (1992). Because the interaction of the crown ether with the ion involves little change in the conformation of the extractant molecule, the energetics of extraction are somewhat more favorable.

Other workers concluded that it was not possible to extract cesium ions into an acceptable diluent using crown ethers alone from a medium containing high concentrations of mineral acids, despite the improved energetics. Gerow et al., *Sep. Sci. Technol.*, 16(5):519–548 (1981); Schulz and Bray, *Sep. Sci. Technol.*, 22:191 (1987).

Several approaches have been taken in the art to enhance the liquid/liquid separation of cesium ions from acidic media by crown ethers. These approaches usually involve providing an organophilic counterion in some form to balance the charge of the cesium ion in the organic phase, thereby avoiding the need to transfer an inorganic anion and its associated water molecules from the aqueous phase. Two approaches involving providing an organophilic counterion in some form are discussed below, as is one other approach.

One approach to enhance cesium ion extraction by crown ethers is to attach proton-ionizable groups to the crown ethers to produce a molecule which is both a coordinator and a counterion. Strzelbickl and Bartsch, *Anal. Chem.*, 53, 1894 (1981); Brown and Bartsch, "Ion Extraction and Transport by Proton-Ionizable Crown Ethers" in *Inclusion Aspects of Membrane Chemistry*, T. Osa and J. L. Atwood, eds., Kluwer Academic Publishers (Boston: 1991), pp. 1–57. A disadvantage of this approach is that the proton-ionizable crown ethers described thus far, for example, are unsuitable for extractions involving strongly acidic aqueous phases because they are in protonated form under those conditions instead of anionic form. Schulz and Bray, *Sep. Sci. Technol.*, 22:191 (1987). Another disadvantage is the difficulty in synthesizing the crown ethers with bonded proton-ionizable groups.

Another approach to enhance cesium ion extraction by crown ethers involves using high molecular weight organic acids (that have inherent extractant capability) along with a crown ether in the diluent. Kinard, et al., *Sep. Sci. Technol.*, 15:1013 (1980); Kinard and McDowell, *J. Inorg. Nucl. Chem.*, 43:2947 (1981); McDowell, et al., *Solvent Extr. Ion Exch.*, 4:217 (1986); Shuler, et al., *Solvent Extr. Ion Exch.*, 3:567 (1985); McDowell, et al., *Anal. Chem.*, 64:3013 (1992); and McDowell, et al., *Sep. Sci. Technol.*, 18:1483 (1983). A disadvantage of the organic acid approach is that, although combinations of organic acids and crown ethers sometimes permit satisfactory cesium ion extraction, they often fail to permit the complete recovery of the cesium ions. Schulz and Bray, *Sep. Sci. Technol.*, 22:191 (1987). A practical drawback is the complicated chemistry involved with multiple extractants, resulting in limited extraction efficiency at high acidity and inefficient cesium ion recovery.

Regarding the selection of the crown ether extractant, the art has made several general observations: (i) that branched side chains on crown ether benzo derivatives increase the solubility of the extractant in the organic phase (Gerow et al., *Sep. Sci. Technol.*, 16(5):519–548 (1981)); (ii) that increasing the side chain length on crown ether benzo derivatives tends to increase their solubility in the organic phase up to 7 carbons in length, but decreases the solubility in the organic phase when the side chain length is more than 7 carbons (Gerow et al., *Sep. Sci. Technol.*, 16(5):519–548 (1981)); (iii) that the strongest ion binding by a crown ether occurs when the ion fits best into the crown ether cavity, unless a "sandwich" complex is formed (two crown ethers to one metal ion) (McDowell, et al., *Anal. Chem.*, 64:3013–3017 (1992)); (iv) that 21-crown-7 is the appropriate size for cesium ions (McDowell, et al., *Anal. Chem.*, 64:3013–3017 (1992)); and (v) that dibenzo crown ethers are selective for alkali metals (such as cesium), whereas dicyclohexano crown ethers are selective for alkaline earth metals (such as strontium) (McDowell, et al., *Anal. Chem.*, 64:3013–3017 (1992)).

McDowell et al., *Anal. Chem.*, 64:3013–3017 (1992), reported that bis-4,4'(5')-(t-butyl benzo)-21-crown-7 (Compound I8, below) yields satisfactory cesium ion extraction ($D_{Cs} \cong 100$) from acidic nitrate media (approximately 0.1M $HNO_3$) by a synergistic effect when combined with an appropriate cation exchanger (a lipophilic counterion, such as didodecylnaphthalene sulfonic acid) in toluene. Dicyclohexano-18-crown-6 also extracted cesium ions from acidic aqueous solution in the same extraction system, but the cesium ion distribution ratio was lower ($D_{Cs} \cong 43$ at 0.1M $HNO_3$). McDowell, et al., *Anal. Chem.*, 64:3013–3017 (1992).

Compound I8 has the bis-4,4'(5')-(benzo)-18-crown-6 backbone structure of Formula I, with the benzo substituent side chain X structure of Formula 8, where the wavy line denotes the bond to the benzo ring.

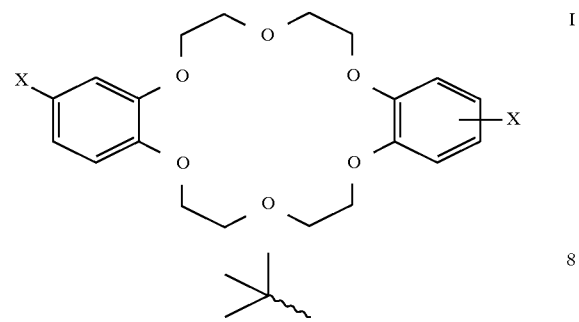

Gerow et al., *Sep. Sci. Technol.* 16(5):519–548 (1981), reported the extraction of cesium ions from aqueous nitric acid media using the macrocylic polyether, bis-4,4'(5')-(1-hydroxyheptyl-benzo)-18-crown-6. Those authors concluded that the crown compound alone was not a sufficiently strong complexing agent to extract cesium ions from an acidic aqueous medium containing inorganic anions such as nitrate or chloride. However, when a large organic counterion, such as didodecylnaphthalene sulfonic acid or di-2-ethylhexyl phosphoric acid was included in the organic phase, cesium ions could be extracted from a 3M nitric acid solution.

Davis, Jr. et al., U.S. Pat. No. 4,749,518 report the addition of bis-4,4'(5')-(1-hydroxyheptyl)-benzo)-18-crown-6 to enhance cesium ion extraction by a cation exchanger (didodecylnaphthalene sulfonic acid or dinonylnaphthalene sulfonic acid at 5 volume percent) in an organic diluent (27–50 volume percent tri-n-butyl phosphate and 68–45 volume percent kerosene) for the separation of cesium ions from aqueous acidic solutions. Davis, Jr. et al., above, reported cesium ion distribution ratios of about 1.5 for bis-4,4'(5')-(1-hydroxyheptyl-benzo) 18-crown-6 ether (0.05M) in the presence of competing ions in an acidic nuclear waste model solution (about 3M $HNO_3$). Those workers reported recovery of up to about 80 percent of the cesium ions from the organic phase through back-extraction into 1M $HNO_3$ aqueous solution. Davis, Jr. et al. also showed that using increasing concentrations of the crown ether increased the distribution ratio.

A disadvantage of the two approaches involving providing an organophilic counterion in some form is that under very acidic conditions, such as nuclear waste processing solutions, the would-be counterions are predominantly in their protonated forms, unable to neutralize the charge of the cesium cation.

A third approach to enhance cesium ion phase transfer using crown ethers was suggested from work with strontium, where it was found that in the presence of substantial quantities of dissolved water in the aliphatic diluent, a lipophilic anion was not required. Horwitz, et al., *Solvent Extr. Ion Exch.*, 8:199 (1990). That report showed that the strontium ion extraction efficiency increased with increasing amounts of water dissolved in the organic phase. Water was effectively dissolved in the organic phase by using any of a variety of oxygenated, aliphatic solutions (e.g. ketones, alcohols) as the organic phase diluent, and equilibrating the organic phase with aqueous solution before use. Horwitz, et al., *Solvent Extr. Ion Exch.,* 8:199 (1990).

The observations with strontium were recently extended to cesium ion extraction. Dietz, et al., *Solvent Extr. Ion Exch.,* 14:1–12 (1996), reported finding that with an appropriate diluent, cesium ions can be extracted from acidic nitrate media using crown ethers in the absence of an organic counterion (either incorporated into the crown ether or as an organic acid in solution). Dietz, et al., studied the cesium ion extraction behavior of bis-4,4'(5')-(t-butyl-benzo) and bis-(cyclohexano) derivatives of 18-crown-6, 21-crown-7, and 24-crown-8. They observed that the cesium ion extraction with Compound I8, bis-(t-butyl-benzo)-18-crown-6, was insensitive to the dissolved water concentration, because a cesium ion is extracted by the crown ether as a 2:1 sandwich complex. Dietz, et al., *Solvent Extr. Ion Exch.,* 14:1–12 (1996).

The oxygenated diluents studied by Dietz, et al., ranged from single functional group alcohols and ketones to carboxylic acids. Dietz, et al., *Solvent Extr. Ion Exch.,* 14:1–12 (1996). Those authors concluded that ketones were the best organic diluent because the cesium ion distribution ratios for the same crown ether were the highest in the ketones, and the crown ether concentrations were higher in the ketones.

An important practical advantage to the approach with crown ether alone over the approach with the added counterion is that the process chemistry using a single extractant is greatly simplified, so that only the nitric acid concentration need be changed to control the cesium ion extraction.

Dietz, et al., above, studied the cesium ion extraction capability of several bis-4,4'(5')-(substituted-benzo)-crown ethers with no added organic acid counterion. Among their other findings, those authors reported that although the bis-substituted-18-crown-6 ethers had higher distribution ratios for cesium ions in the extraction system, the larger crown ethers showed greater cesium selectivity over sodium, superior functional stability, and better compatibility with PUREX-like diluents.

Although the need for improved methods for the removal and recovery of radioactive cesium ions from acidic nuclear waste streams has long been apparent, most of the cesium ion extraction systems studied to date are likely to be of only limited practical value, for various reasons. For example, the physical and chemical properties of certain oxygenated, aliphatic diluents preclude their use in process-scale applications (e.g. the flash point of methyl isobutyl ketone). Further, the aliphatic crown ethers that are readily soluble in oxygenated, aliphatic diluents yield only low cesium ion distribution ratios (e.g. di-cyclohexano-18-crown-6 $D_{Cs} \cong 0.1$ in the absence of organophilic counterion). Still further, the aromatic crown ethers that provide more efficient cesium ion extraction have limited solubilities in oxygenated, aliphatic diluents.

Therefore, there remains a need for cesium ion extraction systems that combine an efficient and selective cesium ion extractant with a diluent possessing satisfactory physical and chemical properties that meet the criteria discussed above. The discussion that follows provides one solution to the cesium ion separation problem.

BRIEF SUMMARY OF THE INVENTION

The present invention relates to a crown ether cesium ion extractant, a process of making the crown ether cesium ion extractant, a process of recycling the crown ether cesium ion extractant, and a separation and recovery process that effectively separates and recovers cesium ions from acidic aqueous solutions, even those containing a variety of other ions such as hydrogen(+1), aluminum(+3), boron(+3), calcium(+2), flouride(−1), iron(+3), nitrate(−1), sodium(+1), strontium(+2), and zirconyl(+2), particularly cations.

The convention used herein for naming structural formulae and compounds is that the bis-(benzo)-18-crown-6 ether backbone corresponds to either Formula I or Formula II (shown below). In the formulae below, X designates the benzo substituents of Formula I and R or R' designate the benzo substituents of Formula II. The benzo substituent formulae are designated with either numerals (for Formula I benzo substituents X) or letters (for Formula II benzo substituents R or R'). The compound names then identify both parts of the formula referred to, for example, Compound I3 or Compound IIF. The benzo substituents are occasionally referred to individually. General formulae also identify both parts of the formula referred to, for example, compound of Formula I2 or Formula II(B–D).

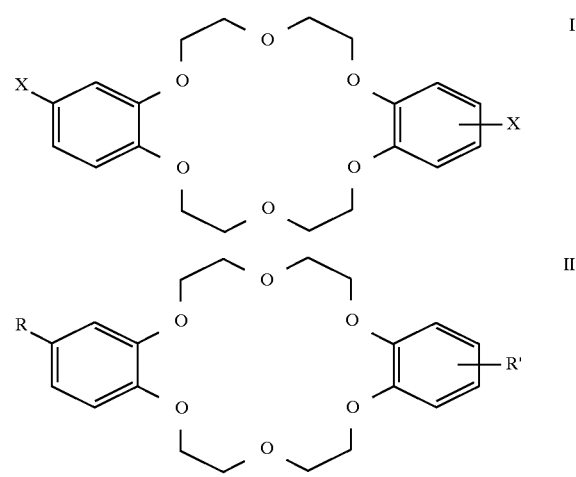

A cesium species contemplated by the present invention is the cesium cation, $Cs^{+1}$. Although an ion, the contemplated cesium species is occasionally referred to hereinafter simply as "cesium" for greater ease in expression, with the understanding that $Cs^{+1}$ is intended. It is also noted that cesium ions are present with an accompanying anion, such as chloride or nitrate, that is other than a large organic anion (organophilic counterion), but reference to that anion is usually omitted and its presence should be inferred.

A crown ether cesium ion extractant of the invention is an acid-catalyzed rearrangement product of a bis-4,4'(5')-[(1-hydroxyalkyl)benzo]-18-crown-6 ether of Formula I wherein X denotes a 1-hydroxyalkyl benzo substituent of Formula 1 (compound of Formula I1) or a 1-(2-hydroxyethyl)ether derivative thereof of Formula 2 (compound of Formula I2):

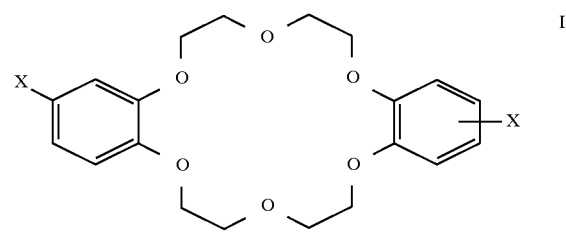

-continued

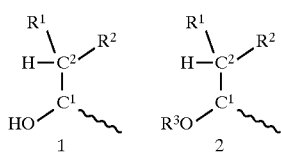

The 1-hydroxyalkyl group of X is a $C_6$–$C_{12}$ benzo substituent that can also be named a 1-hydroxy-$C_6$–$C_{12}$-alkyl benzo substituent positioned at the 4- and 4'(5')-positions of the illustrated benzo rings. The $R^1$ and $R^2$ groups bonded to the second carbon distal from the benzo ring, $C_2$, are individually H or, preferably, a $C_1$–$C_9$ alkyl group. The $R^3$ group in compound of Formula I2 is a 2-hydroxyethyl group, or a chain of such ether groups, such that $R^3$ is —$(CH_2CH_2O)_nH$, wherein n is 1, 2 or 3. Of course, when n is zero, compound of Formula I2 is compound of Formula I1.

A crown ether cesium ion extractant of the invention is a bis-4,4'(5')-(hydroxyalkyl-benzo)-18-crown-6 ether of Formula II:

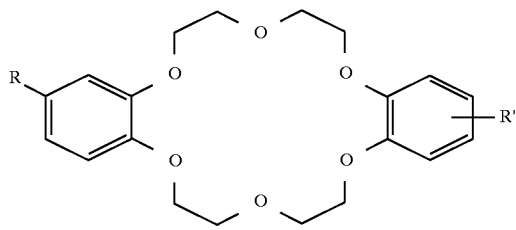

wherein R and R' are positioned at the 4- and 4'(5')-positions of the illustrated benzo rings. Each of R and R' is a $C_6$–$C_{12}$ hydroxyalkyl benzo substituent thought to have a structure corresponding to Formulae A–D, wherein the hydroxyl group of at least one of R and R' is located two carbon atoms distal from the benzo ring, as in Formulae B–D.

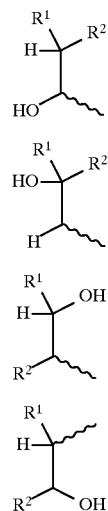

In Formulae A–D, $R^1$ and $R^2$ are individually H or preferably $C_1$–$C_9$ alkyl groups.

An acid-catalyzed rearrangement is also contemplated that is carried out by the following process. A compound of Formula I1 or Formula I2 is dissolved into a water-immiscible organic solvent, forming an organic solution. The organic solution is then contacted with an aqueous solution of about 1M to about 6M mineral acid having a p$K_a$ of about 2 or less to form a reaction mixture containing an aqueous phase and an organic phase. After the reaction mixture has been maintained, and preferably agitated, for a time period sufficient for the acid-catalyzed rearrangement of at least one of the X groups, the formed aqueous and organic phases are separated. The crown ether cesium ion extractant of the invention that is present in the organic phase can be recovered therefrom, or used dissolved directly in that organic solvent or in a diluted form of that solvent to form an organic decontamination phase for a cesium ion extraction process as is discussed below.

A crown ether cesium ion extractant described before can be used to separate cesium ions from an acidic aqueous solution by admixing the acidic aqueous solution containing cesium ions with an organic solution containing the crown ether cesium ion extractant. The organic solution comprises the crown ether cesium ion extractant dissolved or dispersed in an organic solvent, preferably including an aliphatic hydrocarbon diluent. The cesium ion extractant is present at a concentration up to the level of its dispersability or solubility and is preferably at about 0.05M to about 0.5M. The admixture is maintained, preferably with agitation, for a time period sufficient to permit cesium ion and the crown ether cesium ion extractant to complex and form a cesium ion complex-containing organic recovery phase and a cesium ion-depleted aqueous phase. The organic recovery phase and cesium depleted aqueous phase are then separated, thereby removing the cesium ions from the aqueous solution.

The crown ether cesium ion extractant can be recycled, and the cesium ions recovered, by back-extraction of cesium ions from the organic recovery phase containing the crown ether cesium ion extractant complex using a dilute aqueous mineral acid solution, as follows. An organic recovery phase solution containing crown ether cesium ion extractant complexed with cesium ions is admixed with an aqueous phase that is water or water containing about 0.001M to about 1M mineral acid having a p$K_a$ of about 2 or less to form an extraction mixture. The extraction mixture is maintained, preferably with agitation, for a time period sufficient for the cesium ions to dissociate from the crown ether cesium ion extractant complex and equilibrate with the aqueous phase, after which the equilibrated organic and aqueous phases are separated. The equilibrated aqueous phase contains recovered cesium ions. The equilibrated organic phase contains recycled crown ether cesium ion extractant and a lessened amount of cesium ions.

The present invention has several benefits and advantages.

One benefit of the invention is that it provides a new, effective extractant for recovering cesium ions from aqueous acidic wastes.

An advantage of the invention is that it provides a simple, effective extraction process that utilizes that extractant.

Another benefit of the invention is that a contemplated cesium ion extractant and process of using the same is effective for cesium ion removal at relatively high acid concentration.

Another advantage of the invention is that the extraction process does not require the use of an organophilic counterion for the cesium ion.

Yet another advantage of the invention is that extracted cesium ions can be readily recovered from the extractant, permitting recovery of cesium ions in an aqueous medium, and the re-use of the extractant.

Yet another benefit of the invention is that a contemplated cesium ion extractant and process of using the same is effective for cesium ion removal in the presence of a wide variety of cations.

A still further advantage of the invention is that a contemplated cesium ion extractant and process of using the same can discriminate between cesium and sodium ions, and separate cesium ions from an aqueous solution that also contains sodium ions.

Still further benefits and advantages of the invention will be apparent to a skilled worker from the discussion that follows.

BRIEF DESCRIPTION OF THE DRAWINGS

In the drawings forming a portion of this disclosure.

DETAILED DESCRIPTION OF THE INVENTION

The Crown Ether Cesium Ion Extractant

Figure 1:
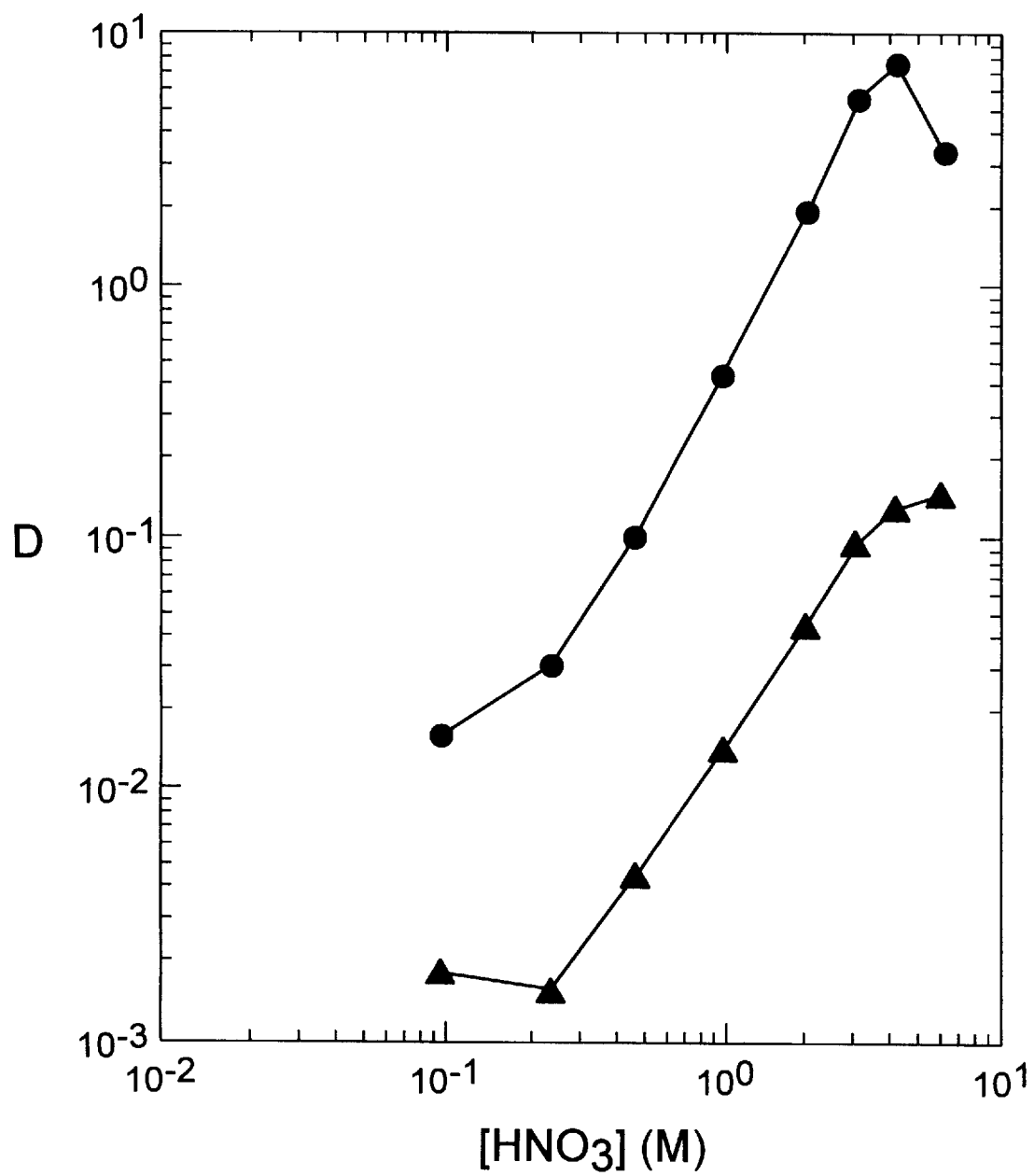
FIG. 1 is a graph that shows the distribution ratio, D, as a function of the nitric acid concentration for the extraction of cesium ions (circles) and sodium ions (triangles) by a contemplated cesium ion extractant that is the acid-catalyzed rearrangement product of Compound I3 in tri-n-butyl phosphate, as discussed in Example 2.

A crown ether cesium ion extractant of the invention is based on an 18-crown-6 ether, despite the general observations regarding the selection of the crown ether extractant teaching toward the use of 21-crown-7 ethers for cesium ion extractants. 18-Crown-6 ethers used in the past for cesium ion extraction formed 2:1 molar (sandwich) complexes (two crown ethers to one cesium ion). Contrarily, an 18-crown-6 ether cesium ion extractant of this invention forms a 1:1 molar complex with cesium ions, whereas its precursor crown ether formed a sandwich complex with cesium ions.

A compound of Formula I1, below, undergoes an acid-catalyzed rearrangement of the X group to form a crown ether extractant of the invention, which is a more efficient cesium ion extractant than is a compound of Formula I1. Formula 1 denotes the general chemical formula of the 1-hydroxy-alkyl-benzo substituent, X.

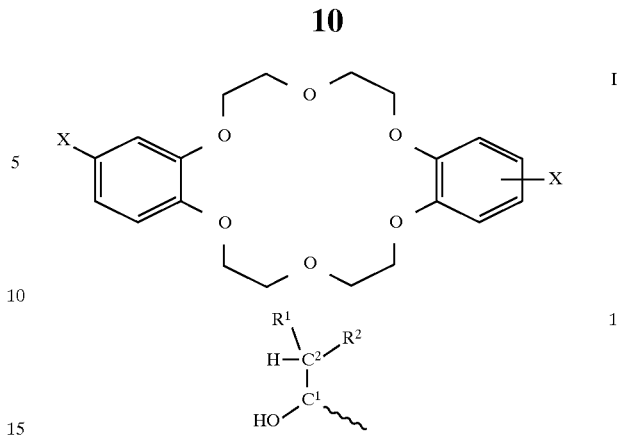

The total number of carbon atoms in substituent 1 is 6–12, preferably 7–10, and most preferably 8. The solubility of the contemplated crown ether cesium ion extractant in organic solvents compatible with the PUREX process increases as the chain length increases up to 7 carbon atoms and decreases thereafter. The solubility of the crown ether also increases when X is a branched hydroxyalkyl group. $R^1$ and $R^2$ are individually H, or, preferably, a $C_1$–$C_9$ alkyl group. Most preferably, $R^1$ and $R^2$ are each a $C_2$–$C_7$ alkyl group that can be the same, but are preferably different. Exemplary $R^1$ and $R^2$ alkyl groups include methyl, ethyl, propyl, i-propyl, butyl, i-butyl, pentyl, hexyl, heptyl, octyl, nonyl and the like.

The hydroxyl group of X is bonded to the first carbon distal from the benzo ring, $C^1$ (the benzylic carbon), in a compound of Formula I1. $R^1$ and $R^2$ of a compound of Formula I1 are bonded to the second carbon distal from the illustrated benzo ring, $C^2$. $C^2$ of a compound of Formula 1 substituent must also have at least one bonded hydrogen (H).

A compound of Formula I2, below, is a 1-(2-hydroxyethyl) ether derivative of compound of Formula I1. In compound of Formula I2, X is a (2-hydroxyethyl) ether of a Formula 2 substituent, wherein $R^3$ is —$(CH_2CH_2O)_n$H and n is 1, 2, or 3. When n is zero, a compound of Formula I2 becomes a compound of Formula I1, so that n can be zero, 1, 2 or 3. In Formula 2, $C^2$ must also have at least one bonded hydrogen (H).

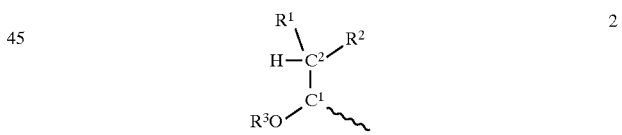

Analogous to an acid-catalyzed rearrangement mechanism for a compound of Formula I1 involving the protonated hydroxyl group at $C^1$ as a leaving group generating a resonance-stabilized benzylic carbocation, a (2-hydroxyethyl) ether group of a compound of Formula I2 can form an alcohol leaving group when protonated, thereby generating the same resonance-stabilized benzylic carbocation and giving rise to a rearranged crown ether cesium ion extractant of the invention. In such a manner, a compound of Formula I2 changes to a compound of Formula I1 as an intermediate in forming a contemplated crown ether cesium ion extractant.

The solvents, catalysts and conditions for the acid-catalyzed rearrangement reaction are discussed in detail hereinafter.

The crown ether cesium ion extractants of the invention can be synthesized from the commercially available bis-benzo-18-crown-6 ether (Aldrich Chemical Company, Inc., Milwaukee Wis.) by a two-step method of Bradshaw et al., Stott et al., *J. Org. Chem.,* 45:4716 (1980); Parish et al., *J. Org. Chem.,* 43:4577 (1978). Briefly, bis-benzo-18-crown-6 ether is diacylated by reaction with Eaton's reagent (Aldrich Chemical Company, Inc., Milwaukee Wis.) and the appropriate carboxylic acid. Reduction of the bis-4,4'(5')-(1-ketoalkyl-benzo)-18-crown-6 ether with sodium borohydride in ethanol gives the corresponding compound of Formula I1.

The corresponding ether derivatives of Formula I2 can be prepared by reaction of the compound of Formula I2 with a catalytic amount of sulfuric acid and an excess of ethylene glycol in dichloromethane at room temperature. Any traces of either calcium or sodium ion in the synthesized crown ethers should be removed by dissolving the crown ether product in methylene chloride and thoroughly washing with either water or dilute hydrochloric acid prior to use.

A contemplated crown ether has been prepared by acid-catalyzed rearrangement of a compound of Formulae I1 or I2, as shown with the 1-hydroxy-2-ethylhexyl crown ethers, Compound I3 and its ether derivatives, Compounds I4 and I5 in Example 1 and discussed hereinafter. Compound I3 is a compound of Formula I1. As compounds of Formula I2, $R^3$ is —$(CH_2CH_2O)_n$H wherein n is zero, 1 and 2, respectively, for Compounds I3, I4 and I5. The use of Compounds I3, I4 and I5 to make an acid-catalyzed rearrangement product is preferred.

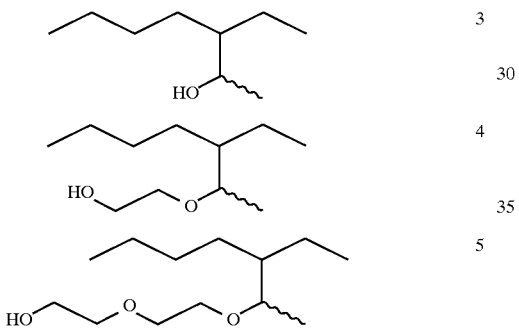

The rearrangement reaction is catalyzed by a mineral acid having a $pK_a$ value of about 2 or less. Univalent mineral acids such as hydrochloric or nitric acid are preferred as compared to multivalent mineral acids such as sulfuric acid. Nitric acid is particularly preferred. When nitric acid is used, a nitrous acid scavenger, such as hydrazine, can be used to minimize the decomposition of the crown ether as described hereinbelow.

The usefulness of an extractant is measured by the distribution ratio, D, of extracted material between the extracting medium and the medium from which the desired material is extracted. Herein, the distribution ratio for cesium ions, $D_{Cs}$, is the concentration of cesium ions in the organic phase divided by the concentration of cesium ions in the aqueous phase. The D values are measured under predetermined, standardized conditions (extraction from a 4M nitric acid solution containing tracer amounts of radioactive cesium ions into an equal volume of a tri-n-butyl phosphate solution of the crown ether), as described hereinafter.

As discussed in Example 1, a compound of Formulae I1 and I2 decompose in the presence of acid, and the decomposition product has a lower cesium ion distribution ratio, $D_{Cs}$, than the starting compound. Such decreases in the $D_{Cs}$ value have typically been used in the art to monitor the decomposition of crown ethers that can extract cesium ions. The acid-catalyzed rearrangement product, the crown ether cesium ion extractants of the invention, have a higher $D_{Cs}$ value than do compounds of either Formula I1 or I2. This crown ether decomposition drives down the $D_{Cs}$ value, while the acid-catalyzed rearrangement of the benzo-substituents of compounds of Formula I1 or I2 drives up the $D_{Cs}$ value for the crown ether that is not decomposed.

A preferred crown ether cesium ion extractant of the invention is a bis-4,4'(5')-(hydroxyalkyl-benzo)-18-crown-6 ether molecule of Formula II:

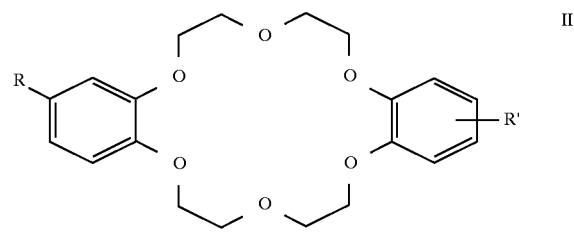

wherein R and R' are positioned at the 4- and 4'(5')-positions of the illustrated benzo rings. Each of R and R' is a $C_6$–$C_{12}$ hydroxyalkyl benzo substituent having a structure corresponding to Formulae A–D. The hydroxyl group of at least one of R and R' is located two carbon atoms distal from said benzo ring, as in Formulae B–D.

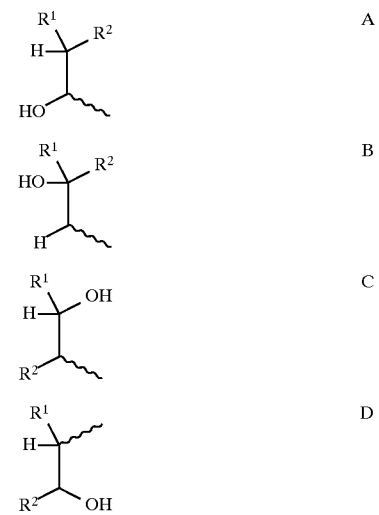

In Formulae A–D, $R^1$ and $R^2$ are individually H or preferably $C_1$–$C_9$ alkyl groups. Further exemplary $R^1$ and $R^2$ group pairs are propyl and methyl; propyl and ethyl; propyl and propyl; butyl and methyl; butyl and ethyl; butyl and propyl; pentyl and methyl; pentyl and ethyl; and hexyl and methyl in the order recited.

A particularly preferred crown ether cesium ion extractant of the invention is a bis-4,4'(5')-(hydroxyoctyl-benzo)-18-crown-6 ether-molecule of Formula II, wherein R and R' are the hydroxyoctyl benzo substituents of Formulae E–H and at least one of R and R' has the Formula F–H. Compounds II(E–H), correspond to the general compounds of Formulae II(A–D) in that $R^1$ is a butyl group ($C_4$) and $R^2$ is an ethyl group ($C_2$).

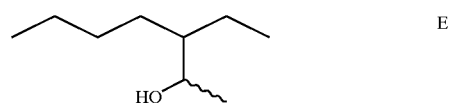

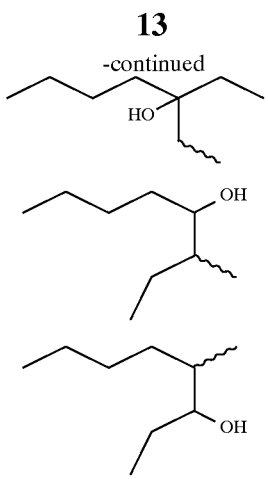

F

G

H

Synthesis of the Crown Ether Cesium Ion Extractant

The present invention provides a process by which at least one of the benzo substituents, X, of a bis-4,4'(5')-(1-hydroxyalkyl-benzo)-18-crown-6, compound of Formula I1, or a (2-hydroxyethyl) ether derivative thereof such as a compound of Formula I2 is rearranged.

The $C_6$ to $C_{12}$ hydroxyalkyl benzo substituent X has a secondary (when either $R^1$ or $R^2$ is H) or, preferably, tertiary (when neither $R^1$ nor $R^2$ is H) carbon $C^2$ adjacent to the benzylic carbon $C^1$ bearing the hydroxyl group. A $C^2$ atom of Formula 1 and 2 substituent must also have at least one bonded hydrogen (H). The acid-catalyzed rearrangement product is a bis 4,4'(5')-(hydroxyalkyl-benzo)-18-crown-6 molecule of Formula II having benzo substituents of Formula A–D, in which at least one of R or R' has the formula of B–D. The hydroxyl group of the rearranged hydroxyalkyl substituent of Formulae B—D is bonded to a carbon atom $C^2$ of R or R' that is two carbon atoms distal from the benzo ring.

A 2-hydroxyethyl ether group bonded to $C^1$ as in a compound of Formula I2 provides the same acid-catalyzed rearrangement product as does a hydroxyl group at $C^1$ as in a compound of Formula I2. Evidence in hand indicates that the ether group is first hydrolyzed to the corresponding alcohol thereby converting a compound of Formula I2 to a compound of Formula I1, which then rearranges to a contemplated cesium ion extractant.

The mineral acid used for catalysis of the rearrangement reaction is the mineral acid described hereinabove, where nitric acid is particularly preferred. When nitric acid is used, a nitrous acid scavenger, such as hydrazine, can be used to minimize the decomposition of the crown ether as described hereinbelow.

Contacting the crown ether with an aqueous mineral acid can also catalyze a decomposition of the crown ether, as noted before, the product of which is not useful as a cesium ion extractant. This decomposition is the basis for the decrease in the cesium ion distribution ratio, $D_{Cs}$, observed at longer rearrangement reaction times as shown in Table 1 of Example 1.

In the case of nitric acid, the decomposition of the crown ether is caused at least in part by the presence of small amounts of nitrous acid. The addition of a nitrous acid scavenger such as hydrazine or sulfamic acid can inhibit this decomposition reaction, while still permitting the acid-catalyzed rearrangement reaction to proceed. Hydrazine in the form of hydrazine dihydrochloride is a particularly preferred nitrous acid scavenger.

The solvent used for the acid-catalyzed rearrangement reaction is a relatively polar, aprotic, organic solvent that is capable of solubilizing the crown ether starting material, water and mineral acid, but is not miscible with water. Exemplary solvents are oxygenated and exhibit dipole moments of about 1.5 to about 4 D (DeBye units).

Water is sparingly soluble in an appropriate organic solvent to the extent of about 0.5M to about 4M (about 0.6 to about 8 weight percent). The solubility of water in various organic solvents under acid-catalyzed rearrangement reaction conditions can be suitably estimated from the scientific literature. See, for example, Riddick & Bunger, *Organic Solvents: Physical Properties and Methods of Purification,* 3rd. Ed., Weissberger, ed., Wiley-Interscience (New York: 1970).

Similarly, mineral acid is dissolved in an appropriate organic solvent at a concentration of about 0.5M to about 5M, depending on the mineral acid concentration in the aqueous phase with which the organic solvent is admixed.

The organic solvent should not itself react with acid or a carbocation intermediate. Therefore protic solvents such as alcohols, carboxylic acids, amines, and some ethers are inappropriate organic solvents. Useful organic solvents are $C_5$–$C_{10}$ ketones, $C_5$–$C_{10}$ ethers, $C_4$–$C_8$ tri-alkyl phosphates and $C_4$–$C_8$ di-alkyl alkyl phosphonates. Exemplary solvents include methyl isobutyl ketone (MIBK), cyclohexanone, 3-pentanone, dipropyl ether, dibutyl ether, i-butyl methyl ether, tri-n-butyl phosphate (TBP), tri-n-propyl phosphate, tri-n-pentyl phosphate, diamyl amyl phosphonate and di-n-butyl butyl phosphonate. MIBK and TBP are the preferred organic solvents for the acid-catalyzed rearrangement reaction.

The reaction can be successfully carried out on any scale. For example, a typical lab-scale reaction used about 5–10 mL organic solvent and 10–20 mL aqueous acid solution.

Cesium Ion Separation Process

The present invention provides a process for the removal of cesium ions from an aqueous solution that also contains other ions, particularly other cations, using a crown ether cesium ion extractant. The cesium ion separation or removal process, that is a liquid/liquid separation or extraction process, is also referred to as a decontamination process because the process can be used to remove radioactive cesium ions from an acidic aqueous solution containing radioactive cesium ions, as well as other radioactive and nonradioactive cations and anions. The steps of the cesium ion removal process include the following manipulations.

First, an organic solution is admixed with an aqueous solution to form an extraction mixture, also referred to herein as an "extraction system of the invention". The extraction mixture has an organic phase containing a crown ether cesium ion extractant and an aqueous phase. The organic solution comprises an organic solvent having the crown ether cesium ion extractant dissolved or dispersed therein. The crown ether cesium ion extractant is present in an amount up to its limit of dispersability or solubility in the organic solvent, and is typically present for most uses at about 0.05M to about 0.5M, and preferably at about 0.05M to about 0.3M. The crown ether cesium ion extractant of the present invention is an acid-catalyzed rearrangement product of a compound of Formula I1 as described hereinbefore. The aqueous solution contains about 1M to about 6M of a mineral acid having a $pK_a$ value of about 2 or less, as well as cesium ions and other ions, particularly cations.

Second, the extraction mixture is maintained for a time period sufficient to form a complex between the cesium ions and the crown ether cesium ion extractant, and form a cesium ion complex-containing organic recovery phase and a cesium ion-depleted aqueous phase. The depletion is measured in comparison to the initially provided aqueous solution where multiple extractions are carried out as in the multi-stage extraction of Example 3. Depletion is measured relative to the cesium concentration of the aqueous phase that initially contacts the organic phase at the start of each extraction step or stage. The maintenance step is preferably accompanied by agitation of the two phases with each other.

Third, the organic recovery phase so formed is separated from the cesium ion-depleted aqueous phase, thereby removing cesium ions from the aqueous solution.

The present invention not only provides a crown ether-based cesium ion solvent extraction process using an extraction system capable of selectively extracting very high percentages of cesium ions from acidic aqueous solutions, but does so with the practical advantage of having simplified process chemistry in that no organophilic counterion need be provided to neutralize the complex of cesium with the crown ether cesium ion extractant in the organic phase.

The extraction of the cesium ions into an organic solution involve the transfer of counterions with the cesium ions from the aqueous phase into the organic phase, as well as transfer of associated water molecules. The solubility of water and/or mineral acid in the organic phase can affect the cesium ion distribution ratio if water and/or mineral acid are involved in the equilibrium.

The $D_{Cs}$ value has usually been found to increase in other extraction systems when the concentration of water dissolved in the organic phase increases. Horwitz, et al., Solvent Extr. Ion Exch., 8:199 (1990); Dietz, et al., Solvent Extr. Ion Exch., 14:1–12 (1996). This effect was observed by those workers for the extraction of cesium ions from acidic aqueous solutions using 21-crown-7 and 24-crown-8 ethers, but the cesium ion extraction with several 18-crown-6 ethers was reported to be essentially independent of the concentration of dissolved water.

The dependence of the cesium ion separation using a crown ether of the invention on the solubility of water in the organic diluent is unclear, but the best cesium ion separation results were obtained with an organic solvent that dissolves about 0.5M to about 4M water and about 0.5M to about 5M mineral acid.

The mineral acid used for the cesium separation is the mineral acid described hereinabove, where nitric acid is particularly preferred. When nitric acid is used, a nitrous acid scavenger, such as hydrazine, can be used to minimize the decomposition of the crown ether as described hereinabove.

The organic solvents that are used for a cesium ion extraction aspect of the invention are immiscible with water and include relatively polar, aprotic solvents. The dipole moments of typical organic solvents range from about 1.5 to about 4 D. Solvents that react with the crown ether cesium ion extractant as the precursor compound of Formula I1 in the presence of acid should be avoided.

Exemplary useful solvents, include ketones, ethers, trialkyl phosphates, and dialkyl alkyl phosphonates. Exemplary organic solvents are those discussed before in regard to synthesis of the crown ether cesium ion extractant. Thus, tri-n-butyl phosphate (TBP) is again a preferred organic solvent.

The concentration of water in the organic phase varied with the amount of acid present in the aqueous phase. The solubility of water in TBP was observed to decrease from about 3.5M for pure water agitated with an equal volume of TBP to about 1M water when a 6M nitric acid solution was agitated with TBP. The nitric acid concentration in the organic phase also depended on the nitric acid concentration in the aqueous phase. The nitric acid concentration in TBP was about 1.5M when a 2M nitric acid solution was agitated with an equal volume of TBP, and reached a high of about 5M when 10–14M nitric acid solution was agitated with TBP.

Undiluted TBP is useful for comparing the extraction behavior of various crown ethers in the cesium ion extraction system of the invention, but its viscosity and water solubility make the use of a mixture of TBP and a low-polarity, kerosene-like diluent (dipole moment of about 0 to about 0.5 D) such as an aliphatic hydrocarbon preferable in an actual process-scale application.

The inclusion of an aliphatic hydrocarbon diluent in the organic solvent confers practical advantages due to favorable physical characteristics of those paraffinic hydrocarbons, such as high flash point and low viscosity. Branched-chain, paraffinic hydrocarbons are preferable to the analogous straight-chain aliphatic hydrocarbon diluents. Examples of a useful commercial paraffinic hydrocarbon mixture are ISOPAR™ L (a mixture of $C_{10}$–$C_{12}$ isoparaffinic hydrocarbons, Exxon Chemical Company, Houston Tex.), ISOPAR™ M (a mixture of isoparaffinic hydrocarbons, Exxon Chemical Company, Houston Tex.), and NORPAR™ (a mixture of normal paraffinic hydrocarbons, Exxon Chemical Company, Houston Tex.).

A phase modifier, such as lauryl nitrile, can be and preferably is included in the organic solvent, preferably up to about 10 volume percent. As the proportion of aliphatic hydrocarbon in the organic solvent increases, the solubility of the crown ether cesium ion extractant and the extractant complex with cesium decrease. The presence of the phase modifier enhances the solubility of the crown ether and of the cesium ion complex with crown ether in the organic solvent, and reduces the likelihood of third phase formation. A phase modifier is an organic liquid that has both polar and long-chain hydrocarbon characteristics, as is well-known. The use of a phase modifier with the aliphatic hydrocarbon diluent permits the concentration of the more polar aprotic solvent such as TBP to be decreased.

For the most efficient cesium ion extraction, the concentration of the crown ether cesium ion extractant should be as high as possible; i.e., up to its limit of solubility or dispersibility. However, the cesium ion extractant can be provided at lower concentrations and still provide a useful cesium ion extraction system. The concentration of a crown ether of the invention is therefore about 0.05M to about 0.5M, and more preferably about 0.05M to 0.3M in the organic phase.

In preferred practice, the aliphatic hydrocarbon diluent constitutes the largest volume percentage of the organic phase used for cesium ion extraction. The polar, aprotic solvent such as TBP or MIBK is present at about 0.5M to about 3M, with an amount of about 1M to about 1.5M being preferred. The phase modifier such as lauryl nitrile is preferably present at about 5 volume percent, and a contemplated crown ether cesium ion extractant is preferably present at about 0.05M to about 0.3M in the diluent.

The aqueous solution of the cesium ion extraction system is the solution from which the cesium ions are desired to be removed. If the aqueous solution is waste from a PUREX-like nuclear fuel reprocessing process, then it contains about 1M to about 6M mineral acid having a $pK_a$ of about 2 or less, and other ions (including radionuclides) in addition to the cesium ions. Details of the PUREX process are provided in U.S. Pat. No. 4,749,518, whose disclosures are incorporated by reference. Similar acid concentrations are found in cesium ion-containing wastes in the non-transuranium element-containing raffinate of a TRUEX extraction process as is disclosed in U.S. Pat. No. 5,100,585, whose disclosures are also incorporated by reference.

The present invention not only provides an alternative crown ether cesium ion extractant, but an extractant that is more efficient at high concentrations of a before-discussed mineral acid in the acidic aqueous solution, such as is found in nuclear waste processing solutions. Nuclear waste processing solutions typically contain about 3M nitric acid.

The extraction system of the present invention is the only extraction system that permits efficient cesium ion extraction from an aqueous solution containing more than about 1M nitric acid. The efficiency of the cesium ion extraction with crown ether cesium ion extractants depends on the concentration of nitric acid in the acidic aqueous solution. The cesium ion distribution ratios tend to increase with increasing concentration of mineral acids up to about 4 or 5M acid.

Cesium ion separation with a contemplated crown ether cesium ion extractant is selective, with the ability to separate cesium ions from an acidic aqueous solution containing a wide variety of other ions.

Several ions in addition to cesium ions, particularly cations that can sometimes be extracted with crown ether extractants, are present in nuclear waste processing solutions. The other ions present include hydrogen(+1), aluminum(+3), boron(+3), calcium(+2), flouride(−1), iron(+3), nitrate(−1), sodium(+1), strontium(+2), and zirconyl(+2) ions. There are few cesium ion extraction systems that separate cesium ions from a solution containing competing cations. Example 3 describes the selective extraction of cesium ions from a nuclear waste model solution containing all of those ions.

The separation factor for cesium ion and a competing ion is the distribution ratio for cesium ion divided by the distribution ratio for the competing ions. The separation factor for cesium over sodium, $\alpha_{Cs/Na}$, is used as a means for evaluating the selectivity of a cesium ion extraction system. As is seen from Example 2, a large separation factor for cesium over sodium is exhibited by a contemplated cesium ion extractant.

In the absence of other ions that can compete with cesium for the crown ether cesium ion extractant, the distribution ratio for cesium ions can be higher than in the presence of competing ions. The separation factor for cesium ions over other ions can vary with the extraction system conditions.

In the contemplated extraction system, a convenient condition variable controlling cesium ion extraction is the concentration of mineral acid. FIG. 1, discussed in Example 2 compares how the cesium ion distribution ratio changes with how a competing ion's distribution ratio changes in response to changing acid concentrations.

FIG. 1 shows that the separation factor for cesium ions over sodium ions increased up to about 4M nitric acid with increasing nitric acid concentration in the aqueous phase. This is thought to be a result of the crown ether coordination of cesium ion versus the competing ion.

The distribution ratio for sodium did not change significantly when the crown ether cesium ion extractant is changed from Compound I3 to the corresponding crown ether cesium ion extractant of the invention, however, the cesium ion distribution ratio increases significantly. The preferred nitric acid concentration for an extraction system of the invention using the acid-catalyzed rearrangement products of Compound I3, Compound I4 and Compound I5 is about 4M for the best cesium ion separation.

The extraction mixture formed by admixture of the organic and aqueous solutions as described before is maintained for a time period sufficient to form a complex between the cesium ions from the aqueous phase and the crown ether cesium ion extractant in the organic phase to form a cesium ion complex-containing organic recovery phase and a cesium ion-depleted aqueous phase. The reaction time for individual complex formation within the organic phase is fairly fast, usually less than one minute being required due to the kinetic lability of the crown ether complex with cesium ions.

The time it takes for an equilibrium distribution of the cesium ions between the organic and aqueous phases is also fairly fast, but is limited by the rate of transfer of the cesium ions across the phase interface. When the extraction mixture is well-agitated, the phase interface surface area is maximized, maximizing the rate of phase transfer of the cesium ions. With the centrifugal extractors of the counter-current mode setup used in Example 3, as are preferred, the contact time required for suitable cesium ion extraction was only about 15 seconds. The extraction mixture can thus be said to be maintained for a time period sufficient to form a cesium ion complex-containing organic recovery phase and a cesium ion-depleted aqueous phase.

Upon formation of the above two phases, the organic recovery phase that contains the cesium ion complex with the extractant and the cesium ion-depleted aqueous phase are separated from each other. That separation of phases in essence completes removal of the cesium ions from the aqueous phase in that any possible reequilibration as into a further diluted or other aqueous phase cannot occur. The before-mentioned centrifugal extraction process is preferred for separating the phases.

Once the phases are separated, the cesium ion-depleted aqueous phase can be further treated to remove other ions or extracted again to further deplete the cesium ion concentration. Multiple extractions on each original acidic cesium ion-containing aqueous solutions are typically preferred, with counter current extraction being a particularly preferred mode of performing the multiple extraction steps. The extractant present in the separated organic recovery phase is typically recycled as is disclosed below.

Recovery of the Cesium Ions and Recycling of the Extractant

The present invention is not only useful for efficiently separating cesium ions from acidic solutions also containing other ions, but doing so in a manner that permits (i) recovery of the cesium ions and (ii) recycling of the crown ether cesium ion extractant. A contemplated process for recycling a crown ether cesium ion extractant comprises the following steps.

First, an organic solution containing a crown ether cesium ion extractant complexed with cesium ions is admixed with an aqueous solution to form an extraction mixture. The extraction mixture thus formed has an organic phase and an aqueous phase. The aqueous solution comprises water or water containing about 0.001M to about 1M of a mineral acid having a $pK_a$ value of about 2 or less, which acids have been discussed before. The organic solution comprises cesium ions complexed with a contemplated crown ether extractant in an organic solvent.

The organic solution utilized in this process is that referred to previously as the separated organic recovery phase. That solution contains a solvent such as TBP or the like, also preferably contains an organic diluent such as a paraffinic hydrocarbon and most preferably also contains a phase modifier such as lauryl nitrile. The complex can be present up to its limit of solubility or dispersibility, and is typically present at up to about 20 percent of the total crown ether cesium ion extractant concentration.

Second, the extraction mixture is maintained for a time period sufficient for the cesium ions to dissociate from said crown ether cesium ion extractant complex and equilibrate with the aqueous phase that contains recovered cesium ions and an equilibrated organic phase that contains the recycled crown ether cesium ion extractant. That maintenance time period is preferably carried out with agitation of the two phases with each other.

Third, the equilibrated organic phase is separated from the equilibrated aqueous phase, thereby recycling the crown ether cesium ion extractant by removing cesium ions from the organic solution. The recycled cesium ion extractant can then be used in its equilibrated organic phase for another extraction, or can be recovered from that solvent.

The product of the before-discussed rearrangement of Compound I3 [shown below] that is FIG. 1 shows the acid dependence of the cesium ion distribution ratio between an aqueous phase of nitric acid and an organic phase of undiluted TBP for a crown ether cesium ion extractant of the invention. The preferred nitric acid concentration for cesium ion recovery from the crown ether cesium extractant used in FIG. 1 is less than about 1M (100M).

For cesium ion recovery and crown ether cesium ion extractant recycling, the aqueous recovery phase is either water or water containing about 0.001 to about 1M mineral acid having a $PK_a$ value of about 2 or less, preferably less than 0.2M acid.

Materials and Methods

A. Reagents

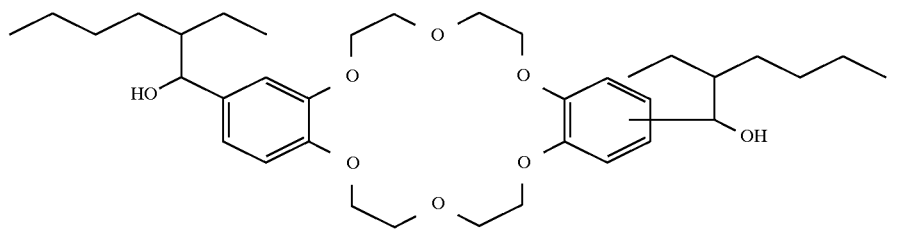

I3 preferably a Compound II(E–H) wherein at least one of R and R' is Formula (F–H) is used in this recycling process, as well as in the previous extraction process.

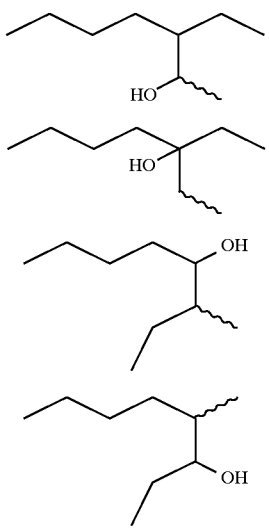

E

F

G

H

The mineral acid, if any, used for the cesium recovery and crown ether cesium ion extractant recycling is the mineral acid described hereinabove. When nitric acid is used, a nitrous acid scavenger, such as hydrazine, can be used to minimize the decomposition of the crown ether as described hereinabove.

The appropriate mineral acid concentrations for cesium ion decontamination of an acidic aqueous solution and for cesium ion recovery from the organic decontamination phase can be determined for a particular organic solvent or diluted organic solvent by the cesium ion radiotracer methods described herein. When the $D_{C_s}$ value is less than one (10°), the conditions are favorable for efficient recovery of the cesium. The mineral acid concentration in the aqueous phase below which the conditions will be favorable for recovery of the cesium ions or recycling of the crown ether cesium ion extractant vary depending on the organic solvent or diluted organic solvent containing the crown ether cesium ion extractant and the cesium ions completed therewith.

All solvents were obtained from Aldrich Chemical Company (Milwaukee Wis.) in the highest purity available, typically >99%. ULTREX™ nitric and hydrochloric acids (J.T. Baker Chemical Company, Phillipsburg N.J.) and MILLI-Q2™ water (Millipore Corp., Bedford Mass.) were used to prepare all acid solutions.

B. Procedures

All cesium ion and sodium ion distribution ratios were measured radiometrically using $^{137}Cs$ ($T_{1/2}$=30.17 years) and $^{22}Na$ ($T_{1/2}$=2.6 years) tracers (Isotope Products Laboratories, Burbank Calif.), respectively. A distribution ratio in a liquid/liquid extraction is the ratio of the concentrations of the ion of interest in the organic phase (org) and the aqueous phase (aq), as shown below for the distribution ratio for cesium ions.

$$D_{Cs} = \frac{[Cs]_{org}}{[Cs]_{aq}}$$

The aqueous solution contains acid and the ions being analyzed (including a tracer radioactive amount). Equal volumes of organic solution and aqueous solution were mixed with a vortex mixer for several minutes, and then centrifuged until phase separation was complete. Aliquots of each phase (usually 100 to 200 μl) were removed for analysis.

The $^{137}Cs$ or $^{22}Na$ activity in each phase was measured by gamma spectroscopy using a COBRA-II AUTO-GAMMA scintillation counter (Packard Instruments, Downers Grove Ill.). Standard, well-known, radiometric assay and counting procedures were employed throughout. Distribution ratios were typically reproducible to within ±5 percent. All measurements were performed at 25°±2° C.

EXAMPLE 1

Synthesis of the Crown Ethers

A weighed quantity of Compound I3, Compound I4, or Compound I5 to be reacted (usually 0.5 to 20 g) was placed in a glass scintillation vial or round bottom flask along with a volume of tri-n-butyl phosphate (TBP) or methyl isobutyl ketone (MIBK) sufficient to yield a solution of the crown ether that would be approximately 0.1M upon complete dissolution of the crown ether. The crown ether/solvent mixture was briefly mixed to initiate the dissolution of the crown ether.

To the crown ether/solvent mixture, was added twice the solvent volume of nitric acid (4M) containing hydrazine dihydrochloride (0.05M) to form the acid-catalyzed rearrangement reaction solution.

The acid-catalyzed rearrangement reaction solution was then placed in a shaking, constant temperature bath at 25° C. for about 24 hours. When lower or higher concentrations of nitric acid were used, the reaction time was lengthened or shortened accordingly. As an alternative to the constant temperature bath, it was found that placing the acid-catalyzed rearrangement reaction solution in a 45° to 50° C. ultrasonic bath for 30 to 90 minutes was also sufficient.

As shown in Table 1, when hydrochloric acid was used as a catalyst under the reaction conditions described above, the cesium ion distribution ratio (0.1M crown ether in TBP, with the cesium ions in a 4M nitric acid solution) was lower than that observed for the rearranged crown ether cesium ion extractant made with nitric acid for the same time of sonication.

TABLE 1

| Sonication Time (hours) | HCl $D_{Cs}$ | HNO$_3$ $D_{Cs}$ |
|---|---|---|
| 0 | 4.92 | 4.92 |
| 0.5 | — | 12.9 |
| 1 | 8.33 | 17.1 |
| 2 | 6.18 | 15.5 |
| 3 | 4.97 | |
| 4 | 4.37 | |

After the acid-catalyzed rearrangement reaction solution reacted for a sufficient time, the rearrangement reaction solution was centrifuged until the organic and aqueous phases were visually separate. The organic phase was drawn off and repeatedly washed with water until all traces of nitric acid were removed, as indicated by a final wash solution pH of about 6. The crown ether cesium ion extractant so prepared could be stored and used in this form. Decomposition of the crown ether was minimized by storing the crown ether cesium ion extractant in the freezer.

When desired, the organic solvent was removed by column chromatography or rotary evaporation (as appropriate), leaving a gelatinous amber solid. The amber solid was dissolved into appropriate solvents to provide an extractant solution. The acid-catalyzed rearrangement reaction product has been prepared in batch sizes of up to 20 grams.

Prior to rearrangement, a solution of Compound I3 or Compound I4 (0.1M) in undiluted TBP yielded a $D_{Cs}$ value of about 4 under the specified, standard conditions (0.1M crown ether in TBP and tracer cesium ions in 4M nitric acid solution). The same concentration of the rearranged crown ether in TBP typically yielded a $D_{Cs}$ value of about 15, although values as high as 45 were observed.

The cesium ion distribution ratio observed prior to rearrangement was in agreement with the literature $D_{Cs}$ value of about 4 reported for Compound I3 by Dietz, et al, *Solv. Extr. Ion Exch.*, 14(3):357–384 (1996). Those workers also reported that the acid-catalyzed decomposition of Compound I3 caused the $D_{Cs}$ value to drop.

Determinations of the mass of the product of the acid-catalyzed rearrangement reaction by Matrix-Assisted Laser Desorption Mass Spectrometry (MALDI-MS) show that the rearrangement product prepared as above and starting from either Compound I3 or either of two (2-hydroxyethyl)ether derivatives thereof (Compound I4 and Compound I5) has the same molecular weight as Compound I3. In general, the acid-catalyzed rearrangement reaction product of a compound of Formula I1 or Formula I2 is therefore an isomer of the precursor compound of Formula I1.

Figure 2:
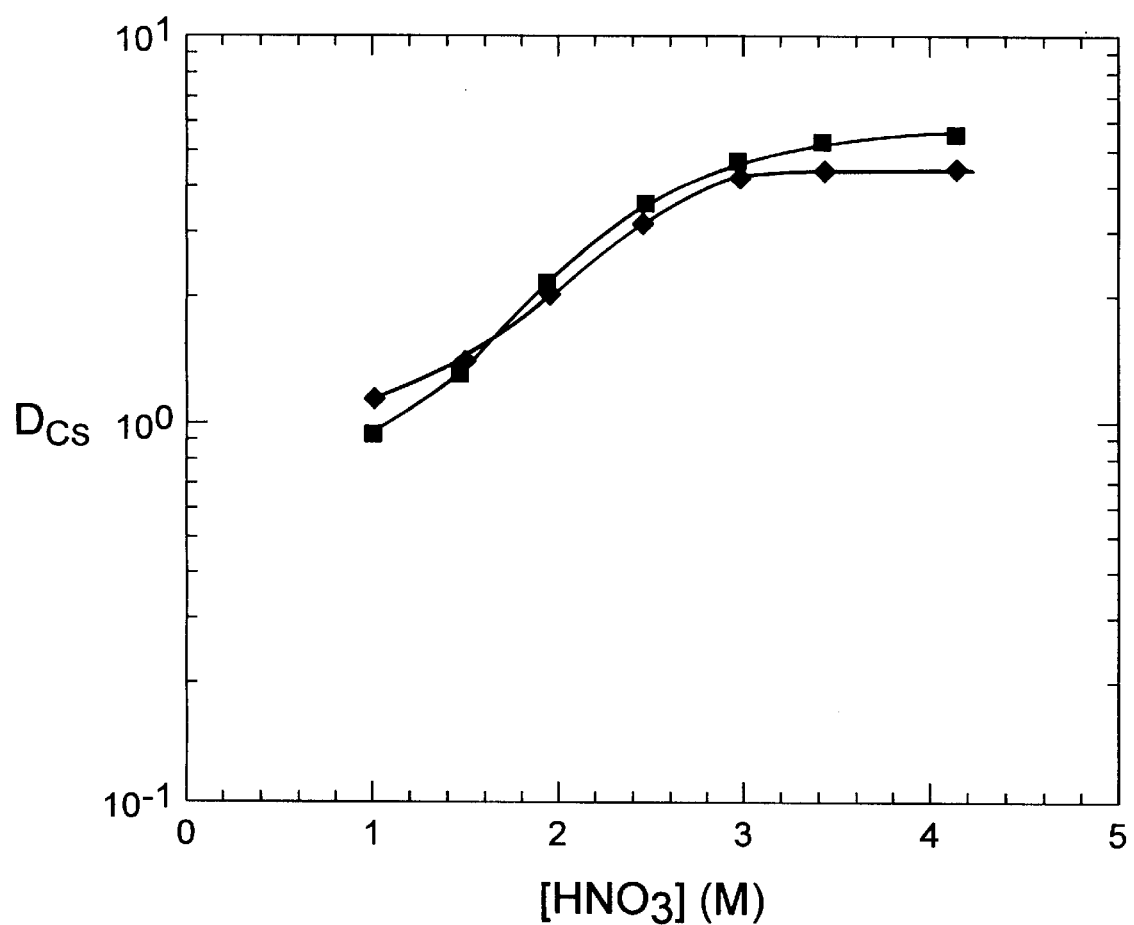
FIG. 2 is a graph that shows that the cesium ion extraction behavior is essentially the same for the extraction by the acid-catalyzed rearrangement products of Compound I4 (squares) and Compound I5 (diamonds) at the various nitric acid concentrations used to catalyze rearrangement, as demonstrated by the distribution ratios, $D_{Cs}$, for cesium ion extraction from 4M nitric acid. These results are discussed in Example 4.

FIG. 2 (discussed in detail in Example 4, below) shows that the cesium ion extraction behavior of the acid-catalyzed rearrangement products of Compound I4 and Compound I5 are essentially the same, supporting the conclusion that the rearrangement products of both Compound I4 and Compound I5 are the same.

Figure 3:
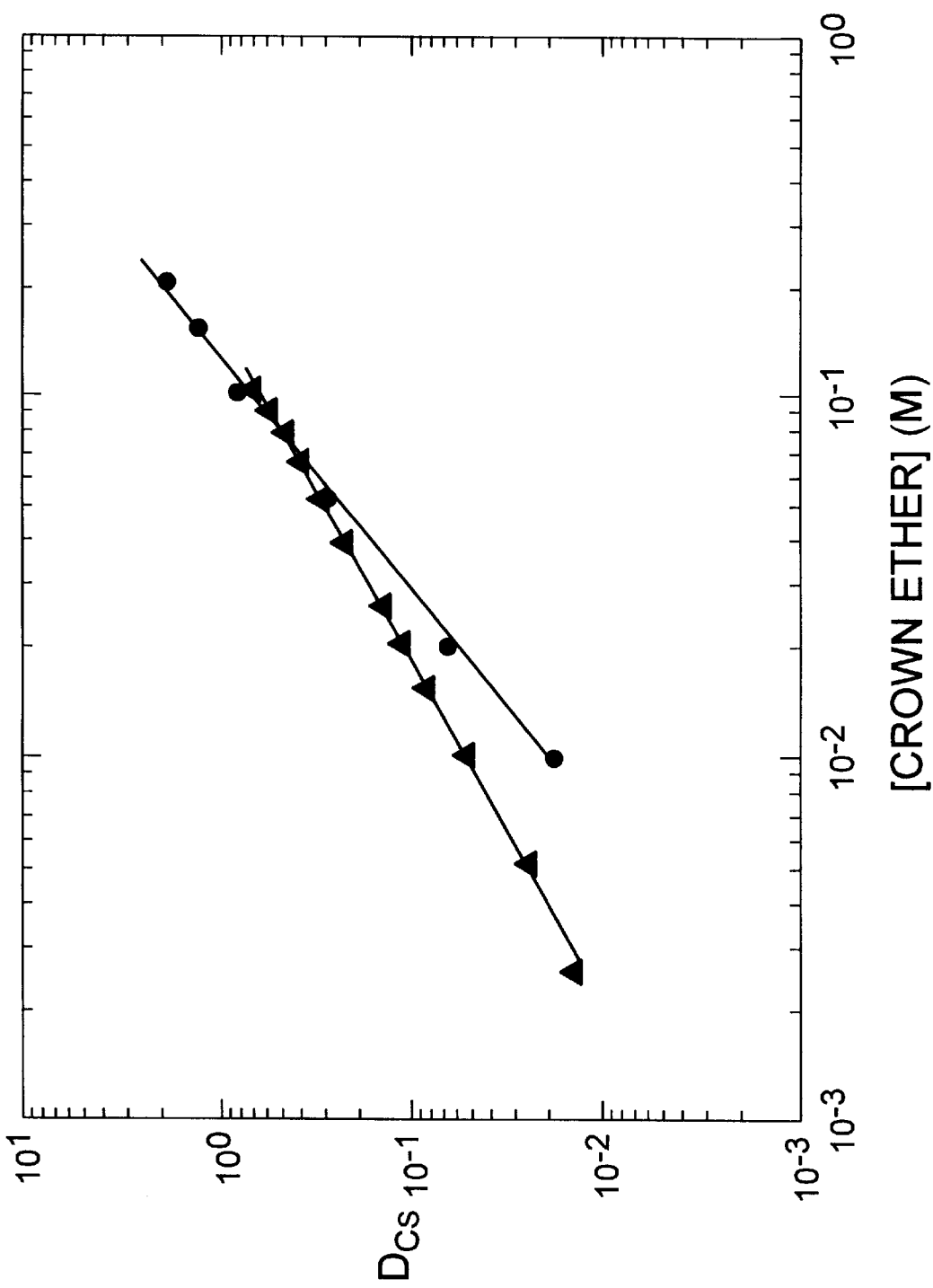
FIG. 3 is a graph that shows the dependence on the cesium ion distribution ratio, $D_{Cs}$, on the crown ether concentration for Compound I3 (circles) and the acid-catalyzed rearrangement product of Compound I4 (triangles), as discussed in Example 5.

FIG. 3 (discussed in detail in Example 5, below) shows that the acid-catalyzed rearrangement product of Compound I4 behaves differently from Compound I3, although both products have the same molecular weight, supporting the conclusion that the acid-catalyzed rearrangement product is an isomer of Compound I3 and not identical to Compound I3.

EXAMPLE 2

Selectivity for Cesium Ions over Sodium Ions

The dependence of selectivity for cesium ions over sodium ions on the aqueous acidity for a crown ether cesium ion extractant of the invention was investigated by individually determining the cesium and sodium distribution ratios ($D_{Cs}$ and $D_{Na}$, respectively) of a solution of a crown ether cesium ion extractant of the invention to calculate a separation factor for cesium ions over sodium ions.

An aqueous solution containing tracer quantities of cesium ions or sodium ions and various concentrations of nitric acid was used as an aqueous phase. Rearranged Compound I3 of Example 1 (0.1M crown ether) was dissolved in a solution of ISOPAR™-L ($C_{10}$–$C_{12}$ isoparaffinic hydrocarbon) containing 1M tri-n-butyl phosphate as an organic phase. The aqueous and organic phases were admixed, maintained with agitation and separated. The results are shown in Table 2 below, and depicted in FIG. 1.

TABLE 2

| [HNO$_3$] (M) | $D_{Cs}$ | $D_{Na}$ | Separation Factor |
|---|---|---|---|
| 0.0955 | 0.016 | 0.002 | 8 |
| 0.241 | 0.032 | 0.002 | 16 |
| 0.476 | 0.10 | 0.005 | 20 |
| 0.986 | 0.45 | 0.015 | 30 |
| 1.93 | 2.1 | 0.049 | 43 |
| 2.96 | 5.6 | 0.10 | 56 |
| 4.13 | 8.0 | 0.14 | 57 |
| 5.88 | 3.5 | 0.16 | 22 |

As is seen, the nitric acid dependency of the cesium ion distribution ratio, $D_{Cs}$, increased as the acid concentration was raised, then declined above about 4M HNO$_3$. The nitric acid dependency of the sodium ion distribution ratio, $D_{Na}$, generally increased as the acid concentration was raised. The distribution ratio for cesium ions was higher than that for sodium ions, so the separation factor for cesium ions over sodium ions ($D_{Cs}/D_{Na}$) was always greater than one. As a result of the steeper increase of $D_{Cs}$ as compared with the increase $D_{Na}$ on the nitric acid concentration between about 0.2M HNO$_3$ and about 3M HNO$_3$, the separation factor increased greatly over that range.

At about 0.1M $HNO_3$, $D_{Cs}$ is much less than one, which means that the distribution of cesium ions between the organic phase and the aqueous phase is heavily weighted toward the aqueous phase. However, at about 4M $HNO_3$, the distribution of cesium ions is heavily weighted toward the organic phase.

As a result of the acid dependence of the extraction system, in the procedure outlined in Example 3, below, the cesium ion extraction from the aqueous phase was carried out at 4M $HNO_3$, and the recovery of cesium ions from the organic extractant was carried out in a 0.1M $HNO_3$ aqueous solution.

EXAMPLE 3

Procedure for Cesium Ion Separation Using the Acid-Catalyzed Rearrangement Product of Compound I3

A. Preconditioning of the Extraction System

The crown ether cesium ion extractant used in this example was a nitric-acid catalyzed rearrangement product of Compound I3. One volume of the extractant solution [0.1M crown ether, 1.2M tri-n-butyl phosphate (TBP), and 5 percent (V/V) lauryl nitrile in ISOPAR™-L, a $C_{10}$–$C_{12}$ isoparaffinic hydrocarbon solvent] forming the organic preconditioning phase was contacted with two volumes of an aqueous nitric acid solution (4M $HNO_3$) forming the aqueous preconditioning phase. The organic and aqueous preconditioning phases were separated and the preconditioning step was repeated on the organic preconditioning phase to ensure equilibration of the organic phase with nitric acid to avoid significant decreases of the acid concentration throughout the decontamination ("scrubbing" cesium ion recovery and extractant recycling) steps of the cesium ion extraction.

B. Decontamination of an Aqueous Solution

Cesium ions were extracted from a synthetic model of a high level liquid waste solution (3.78M $H^+$, 0.49M $Al^{3+}$, 0.086M $B^{3+}$, 0.78M $Ca^{2+}$, 1.24M $F^-$, 0.015 M $Fe^{3+}$, 6.4M $NO_3^-$, 0.015M $Na^+$, 0.0039M $Sr^{2+}$, 0.22M $ZrO^{2+}$) containing cesium ions (0.005M $Cs^+$) forming the aqueous decontamination phase by contacting the aqueous phase with two volumes of the preconditioned organic phase containing the crown ether cesium ion extractant (0.1M crown ether). The extraction was carried out in a countercurrent mode using nine extraction stages and two scrub stages to form a contaminated organic recovery phase containing a crown ether complex with cesium ions and a raffinate (cesium ion-depleted aqueous phase) of high-level liquid waste solution that was decontaminated with respect to cesium ions.

The decontamination of (cesium extraction from) the synthetic model of the high level radioactivity liquid waste solution provided a four hundred thousand-fold decrease in the cesium ion concentration in the cesium ion-depleted aqueous phase (raffinate).

C. Recovery of the Cesium Ions and Recycling of the Extractant

Cesium ions were recovered ("stripped") from the contaminated organic recovery phase solution containing the crown ether complex with cesium ions by treating two volumes of the organic recovery phase solution with one volume of a dilute aqueous nitric acid solution (0.1M $HNO_3$) to form an aqueous recovery phase. The aqueous and organic phases were admixed by shaking. The resulting organic recovery phase now relatively depleted of complexed cesium ions was separated from the aqueous recovery phase. This separation resulted in a dilute aqueous acid solution that contained the cesium ions. The recovery process was repeated to completely decontaminate the organic phase containing the crown ether cesium ion extractant, permitting that extractant to be recycled.

Greater than 99.99 percent of the cesium ion amount initially present in the aqueous waste model was present in the pooled aqueous recovery phases of dilute aqueous acid solution containing the cesium ions at the end of this stripping process.

EXAMPLE 4

Comparison of the Cesium Ion Extraction Behavior of the Acid-Catalyzed Rearrangement Products of (2-Hydroxyethyl) Ether Derivatives Compound I4 and Compound I5 were separately dissolved in tri-n-butyl phosphate (0.1M crown ether in 5 mL TBP) in test tubes. Two volumes of nitric acid solution (10 mL of 1–4M nitric acid) were added to each test tube, to form an acid-catalyzed rearrangement reaction admixture of an organic and an aqueous phase. The rearrangement reaction admixtures were agitated at room temperature for 24 hours, then the organic and aqueous phases were separated. The organic phase was washed with water until the pH of the water was about 6.

The cesium ion distribution ratio was determined for the acid-catalyzed rearrangement product using the washed organic phases containing the rearrangement products of Compound I4 and Compound I5 (1 mL, about 0.1M crown ether) to extract tracer amounts of cesium from aqueous solutions containing 4M nitric acid.

The results of the cesium ion distribution ratio measurements are shown in FIG. 2 for the acid-catalyzed rearrangement product of Compound I4 (squares) and the acid-catalyzed rearrangement product of Compound I5 (diamonds) as a function of the nitric acid concentration during the rearrangement reaction. The cesium ion extraction behavior is essentially the same for the two acid-catalyzed rearrangement products.

EXAMPLE 5

Stoichiometry of the Crown Ether Cesium Extractant Complexes with Cesium Ions

The stoichiometry of the crown ether cesium ion extractant complexes with cesium ions were determined by monitoring the dependence of the cesium ion distribution ratio on the concentration of the crown ether cesium ion extractant. The cesium complex stoichiometry of the acid-catalyzed rearrangement product of Compound I4 was compared with the cesium complex stoichiometry of Compound I3.

The acid-catalyzed rearrangement product of Compound I4 was made as described in Example 4, above.

FIG. 3 shows the dependence of the cesium ion distribution ratio on the concentration of the crown ether cesium ion extractants, Compound I3 (circles) and the acid-catalyzed rearrangement product of Compound I4 (triangles). The slope of the line corresponds to the stoichiometry of the complex with cesium.

The determination of the cesium ion distribution ratio was carried out as described in Example 6, below, for the nitric acid dependencies of $D_{Cs}$, except that in the present set of determinations, the nitric acid concentration was held constant at 4.05M, and the crown ether concentration was varied from about 0.002M to about 0.2M.

In the case of Compound I3, the slope of the line is 1.5 ±0.1, so there is more than one crown ether cesium extractant molecule for each cesium ion. This result agrees with the report by Dietz, et al., *Solvent Extr. Ion Exch.*, 14:1–12 (1996) of the formation of a sandwich complex with Compound I3.

In the case of the crown ether cesium ion extractant of the invention, the acid-catalyzed rearrangement product of Compound I4, the slope of the line is 1.07±0.03, so there is only one crown ether cesium extractant molecule for each cesium ion.

Although the acid-catalyzed rearrangement product of Compound I4 has the same molecular weight as Compound I3, the acid-catalyzed rearrangement product of Compound I4 behaves differently from Compound I3, so it is clearly a different molecule.

EXAMPLE 6

Comparison of the Cesium Ion Extraction Behavior of a Contemplated Crown Ether with Crown Ethers of the Art Compound I3 was used in a nitric-acid catalyzed rearrangement process as described hereinabove to make a contemplated crown ether. The cesium ion extraction behavior of the rearranged Compound I3 was compared, as follows, to the crown ethers of the art: Compound I3, Compound I4, and Compound I8.

Compound I8 was obtained from Eichrom Industries, Inc., Darien, Ill.

Compound I3 (commercially available from Eichrom Industries, Darien, Ill.) was synthesized by a two-step method of Bradshaw et al., Stott et al., *J. Org. Chem.*, 45:4716 (1980); Parish et al., *J. Org. Chem.*, 43:4577 (1978). Briefly, bis-benzo-18-crown-6 ether was diacylated by reaction with 2-ethyl hexanoic acid and Eaton's reagent. Reduction of the bis-4,4'(5')-(1-keto-2-ethylhexyl-benzo)-18-crown-6 ether with sodium borohydride in ethanol gave Compound I3.

Compounds I4 and I5 were prepared by reaction of Compound I3 with a catalytic amount of sulfuric acid and an excess of ethylene glycol in dichloromethane at room temperature. Any traces of either calcium or sodium ion in the synthesized crown ethers were removed by dissolving the crown ether product in methylene chloride and thoroughly washing with either water or dilute hydrochloric acid prior to use.

A crown ether (0.1M) was dissolved in undiluted tri-n-butyl phosphate (0.5 mL to 1 mL) in a test tube, forming an organic phase. An equal volume of nitric acid solution containing a tracer amount of cesium-137 constituted an aqueous phase that was added to the test tube. The organic and aqueous phases were maintained by shaking them together at room temperature (25° C.±3° C.) for about a minute, then the phases were separated. Aliquots (100 µL) were taken of each phase. The relative amounts of cesium ion in each phase were determined by scintillation counting as described above, and used to calculate the cesium ion distribution ratio. The process was conducted for several nitric acid concentrations.

Figure 4:
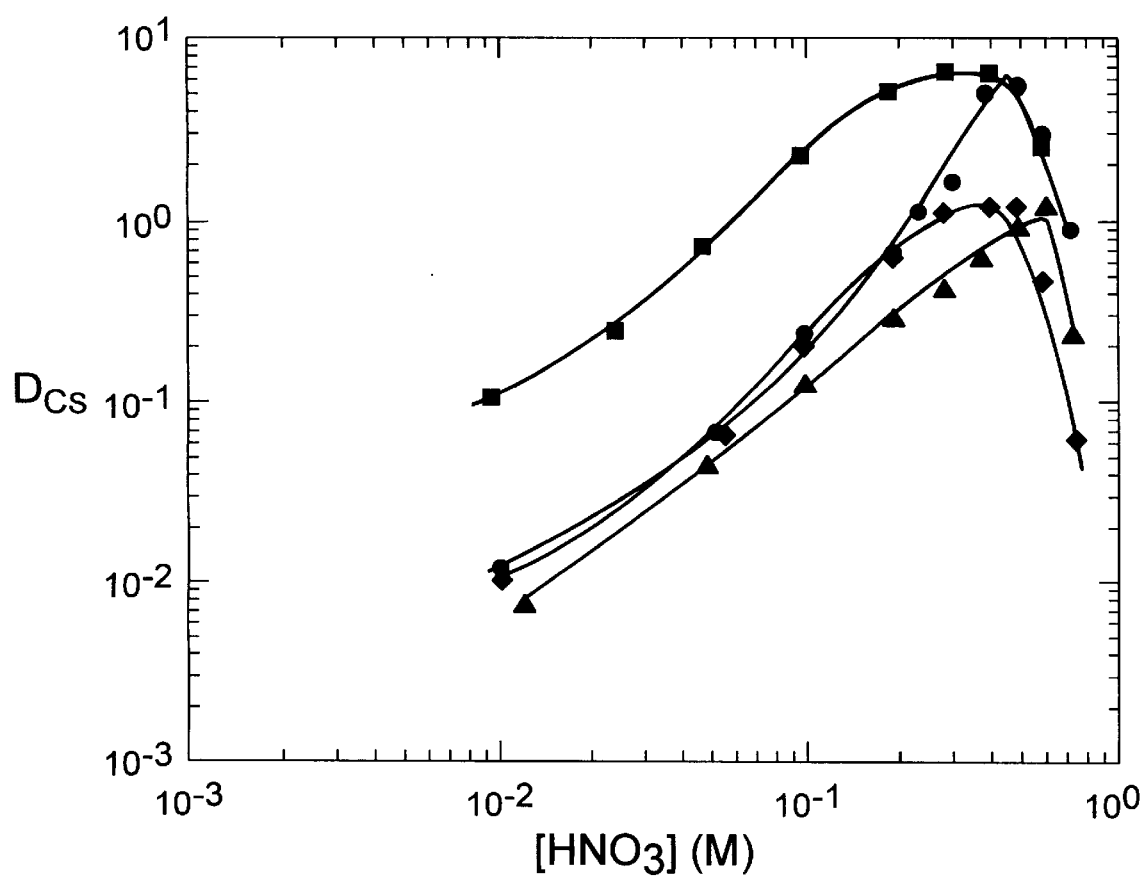
FIG. 4 is a graph that shows the cesium ion distribution ratio, $D_{Cs}$ as a function of nitric acid concentration for the extraction of cesium ions by the prior art compounds, Compound I3 (circles), Compound I4 (triangles), and Compound I8 (diamonds) contrasted with the acid-catalyzed rearrangement product of Compound I4 (squares), as discussed in Example 6.

The nitric acid dependence of the cesium ion distribution ratios for Compound I3 (circles), Compound I4 (triangles), Compound I8 (diamonds), and the acid-catalyzed rearrangement product of Compound I4 (squares) are shown in FIG. 4. The acid-catalyzed rearrangement product of Compound I4 exhibited about a ten-fold higher cesium distribution ratio at all acid concentrations up to about 3M nitric acid than the other three compounds, Compound I3, Compound I4 and Compound I8.

The foregoing description and the examples are intended as illustrative and are not to be taken as limiting. Still other variations within the spirit and scope of this invention are possible and will readily present themselves to those skilled in the art.

We claim:

1. A bis-4,4'(5')-(hydroxyalkyl-benzo)-18-crown-6 molecule of Formula II:

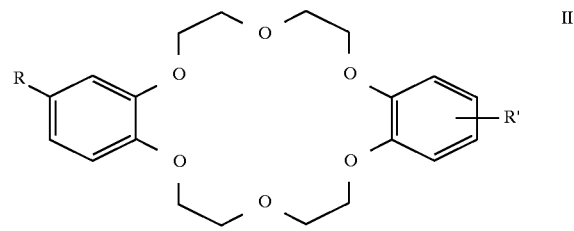

wherein (i) R and R' are positioned at the 4- and 4'(5')-positions of the illustrated benzo rings, (ii) each of R and R' is $C_6$–$C_{12}$ hydroxyalkyl benzo substituent having a structure corresponding to Formulae A–D,

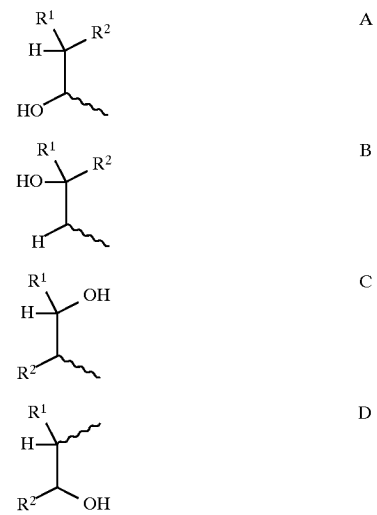

wherein $R^1$ and $R^2$ are individually H or $C_6$–$C_9$ alkyl groups, and (iii) the hydroxyl group of said $C_6$–$C_{12}$ hydroxyalkyl benzo substituent in at least one of R and R' is located two carbon atoms distal from said benzo ring as in Formulae B–D.

2. The bis-4,4'(5')-(hydroxyalkyl-benzo)-18-crown-6 molecule of claim 1 wherein each of R and R' is a hydroxyoctyl benzo substituent.

3. The bis-4,4'(5')-(hydroxyoctyl-benzo)-18-crown-6 molecule of claim 2 wherein each of R and R' has a structure corresponding to Formulae B–D.

4. A process for making a bis-4,4'(5')-(hydroxyalkyl-benzo)-18-crown-6 molecule of Formula II:

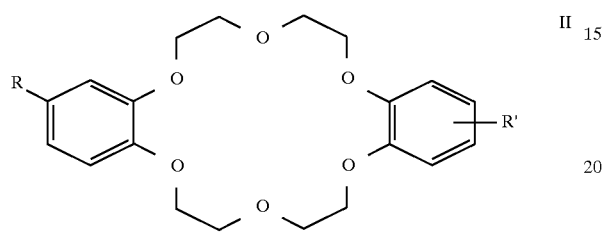

wherein (i) R and R' are positioned at the 4- and 4'(5')-positions of the illustrated benzo rings, (ii) each of R and R' is a $C_6$–$C_{12}$ hydroxyalkyl benzo substituent having a structure corresponding to Formulae A–D,

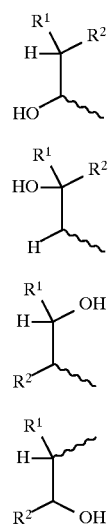

wherein $R^1$ and $R^2$ are individually H or $C_1$–$C_9$ alkyl groups, and (iii) the hydroxyl group of said $C_6$–$C_{12}$ hydroxyalkyl benzo substituent in at least one of R and R' is located two carbon atoms distal from said benzo ring as in Formulae B–D;

said process comprising the steps of:

(a) dissolving a bis-4,4'(5')-[(1-hydroxy-alkyl)benzo]-18-crown-6 of Formula I wherein X is a $C_6$–$C_{12}$ 1-hydroxyalkyl benzo substituent positioned at the 4- and 4'(5')-positions of the illustrated benzo rings having a structure corresponding to Formula 1:

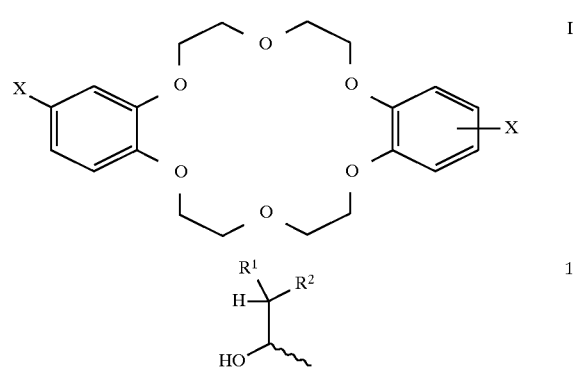

wherein $R^1$ and $R^2$ are individually H or $C_1$–$C_9$ alkyl groups, or a 1-(2-hydroxyethyl)ether derivative thereof, in an aprotic, water-immiscible organic solvent to form an organic solution;

(b) contacting said organic solution with an aqueous solution of about 1M to about 6M mineral acid to form a reaction mixture containing an aqueous phase and an organic phase;

(c) maintaining said reaction mixture for a time sufficient to convert at least one of said X groups having a structure corresponding to Formula 1 into groups having a structure corresponding to Formulae B–D to form a bis-4,4'(5')-(hydroxyalkyl-benzo)-18-crown-6 product of Formula II wherein R and R' have structures corresponding to Formulae A–D; and (d) separating the aqueous phase from the organic phase that contains said bis-4,4'(5')-(hydroxy-alkyl-benzo)-18-crown-6 product of Formula II.

5. The process of claim 4 wherein said organic solvent of step (a) is tri-n-butyl phosphate or methyl isobutyl ketone.

6. The process of claim 4 wherein said reaction mixture is agitated at a temperature of about 18° C. to about 30° C. for a time period of about 10 to about 48 hours.

7. The process of claim 4 wherein the reaction mixture is ultrasonically agitated at a temperature of about 45° C. to about 50° C. for a time period of about 30 to about 90 minutes.

8. The process of claim 4 wherein the separation of step (d) is carried out by:

(i) centrifuging said reaction mixture into distinct organic and aqueous phases; and (ii) drawing off the organic phase.

9. The process of claim 8 including the further step of:

(iii) washing the organic phase with water to remove any remaining mineral acid.

10. The process of claim 4 further comprising the step of:

(e) removing the organic solvent from the bis-4,4'(5')-(hydroxyalkyl-benzo)-18-crown-6 product.

11. A process for the removal of cesium ions from an aqueous solution also containing other ions using a crown ether cesium ion extractant comprising the steps of:

(a) admixing an organic solution containing a crown ether cesium ion extractant with an aqueous solution to form an extraction mixture having an organic phase and an aqueous phase, said organic solution comprising an organic solvent having dissolved or dispersed therein about 0.05M to about 0.5M crown ether cesium ion extractant that is a bis-4,4'(5')-(hydroxyalkyl-benzo)-18-crown-6 molecule of Formula II:

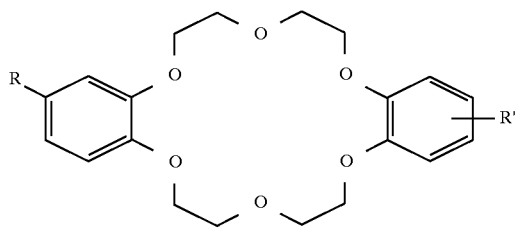

wherein
(i) R and R' are positioned at the 4- and 4'(5')-positions of the illustrated benzo rings,
(ii) each of R and R' is a $C_6$–$C_{12}$ hydroxyalkyl benzo substituent having a structure corresponding to Formulae A–D,

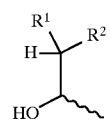 A

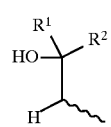 B

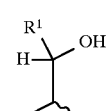 C

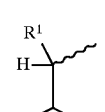 D wherein $R^1$ and $R^2$ are individually H or $C_1$–$C_9$ alkyl groups, and
(iii) the hydroxyl group of said $C_6$–$C_{12}$ hydroxyalkyl benzo substituent in at least one of R and R' is located two carbon atoms distal from said benzo ring as in Formulae B–D, and said aqueous solution containing about 1M to about 6M mineral acid having a $PK_a$ of 2 or less, cesium ions and other ions;
(b) maintaining said extraction mixture for a time period sufficient to form a complex between said cesium ions and said crown ether cesium ion extractant and form a cesium ion complex-containing organic recovery phase and a cesium ion-depleted aqueous phase; and
(c) separating the organic recovery phase from the cesium ion-depleted aqueous phase, thereby removing cesium ions from said aqueous solution.

12. The process of claim 11 wherein said organic solvent comprises tri-n-butyl phosphate.

13. The process of claim 12 wherein said organic solution comprises about 0.5M to about 2.0M tri-n-butyl phosphate organic solvent and up to about 10 volume percent lauryl nitrile in an aliphatic hydrocarbon solvent diluent.

14. The process of claim 11 carried out in countercurrent mode.

15. A process for recycling a crown ether cesium ion extractant comprising the steps of:
(a) admixing an organic solution containing a crown ether cesium ion extractant complexed with cesium ions with an aqueous solution to form an extraction mixture having an organic phase and an aqueous phase, said organic solution comprising cesium ions complexed with a crown ether cesium ion extractant dissolved in an organic solvent, wherein said crown ether cesium ion extractant is a bis-4,4'(5')-(hydroxy-alkyl-benzo)-18-crown-6 molecule of Formula II:

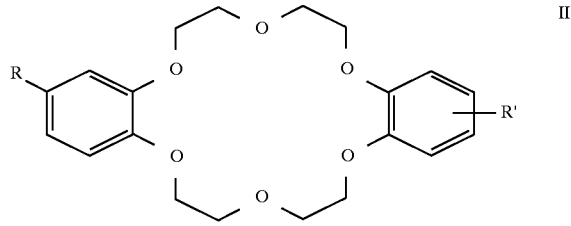

wherein
(i) R and R' are positioned at the 4- and 4'(5')-positions of the illustrated benzo rings,
(ii) each of R and R' is a $C_6$–$C_{12}$ hydroxyalkyl benzo substituent having a structure corresponding to Formulae A–D,

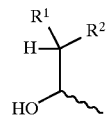 A

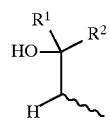 B

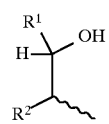 C

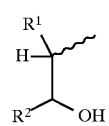 D wherein $R^1$ and $R^2$ are individually H or $C_1$–$C_9$ alkyl groups, and
(iii) the hydroxyl group of said $C_6$–$C_{12}$ hydroxyalkyl benzo substituent in at least one of R and R' is located two carbon atoms distal from said benzo ring as in Formulae B–D, and said aqueous solution comprising water or water containing about 0.001M to about 1M mineral acid having a $pK_a$ of about 2 or less;
(b) maintaining said extraction mixture for a time period sufficient for the cesium ions to dissociate from said crown ether cesium ion extractant complex and equilibrate with the aqueous phase to form an equilibrated aqueous phase containing recovered cesium ions and an equilibrated organic phase containing the recycled crown ether cesium ion extractant; and
(c) separating the equilibrated organic phase from the equilibrated aqueous phase, thereby recycling said crown ether cesium ion extractant by removing cesium ions from the organic solution.

16. The process of claim 15 wherein said cesium ion extractant is an acid-catalyzed rearrangement product of a compound whose structural formula is

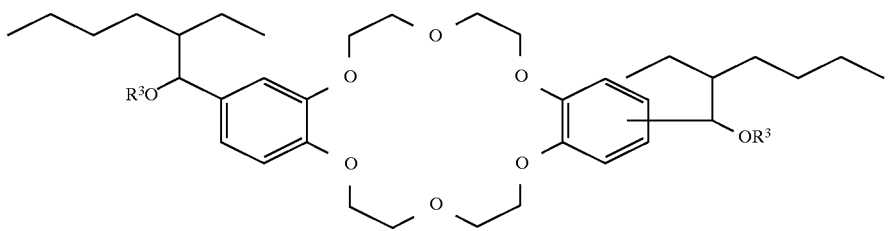

wherein $R^3$ is —$(CH_2CH_2O)_nH$ and n is zero, 1,2 or 3.

17. A process for recovering cesium ions from a crown ether cesium ion extractant complex comprising the steps of:

(a) admixing an organic solution containing a crown ether cesium ion extractant complexed with cesium ions with an aqueous solution to form an extraction mixture having an organic phase and an aqueous phase, said organic solution comprising cesium ions, about 0.05M to about 0.5M crown ether cesium ion extractant and an organic diluent, wherein said crown ether cesium ion extractant is a bis-4,4'(5')-(hydroxy-alkyl-benzo)-18-crown-6 molecule of Formula II:

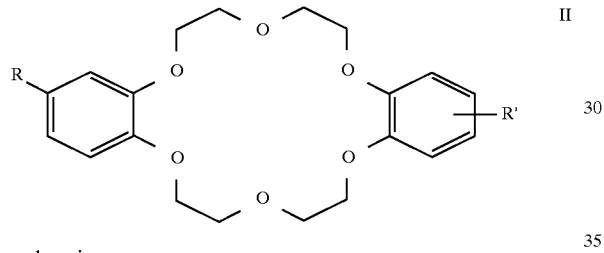

II wherein
(i) R and R' are positioned at the 4- and 4'(5')-positions of the illustrated benzo rings,
(ii) each of R and R' is a $C_6$-$C_{12}$ hydroxyalkyl benzo substituent having a structure corresponding to Formulae A–D,

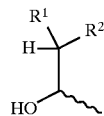

A

-continued

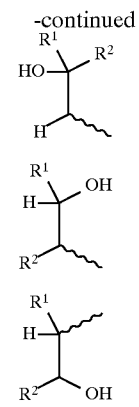

wherein $R^1$ and $R^2$ are individually H or $C_1$–$C_9$ alkyl groups, and
(iii) the hydroxyl group of said $C_6$–$C_{12}$ hydroxyalkyl benzo substituent in at least one of R and R' is located two carbon atoms distal from said benzo ring as in Formulae B–D, and said aqueous solution comprising water or water containing about 0.001M to about 1M mineral acid having a $pK_a$ of about 2 or less;

(b) maintaining said extraction mixture for a time period sufficient for the cesium ions to dissociate from said crown ether cesium ion extractant complex and form a equilibrated organic phase and an equilibrated aqueous phase that contains recovered cesium ions; and (c) separating the equilibrated organic phase from the equilibrated aqueous phase, thereby recovering said cesium ions from the organic solution.

* * * * *